United States Patent
Ko et al.

(10) Patent No.: US 9,370,309 B2
(45) Date of Patent: Jun. 21, 2016

(54) MAGNETOENCEPHALOGRAPHY SYSTEM AND METHOD FOR 3D LOCALIZATION AND TRACKING OF ELECTRICAL ACTIVITY IN BRAIN

(75) Inventors: Harvey W. Ko, Ellicott City, MD (US); Ibolja Cernak, Columbia, MD (US); Michael P. McLoughlin, Sykesville, MD (US)

(73) Assignee: The Johns Hopkins University, Baltimore, MD (US)

( * ) Notice: Subject to any disclaimer, the term of this patent is extended or adjusted under 35 U.S.C. 154(b) by 366 days.

(21) Appl. No.: 13/885,746

(22) PCT Filed: Nov. 18, 2011

(86) PCT No.: PCT/US2011/061455
§ 371 (c)(1),
(2), (4) Date: May 16, 2013

(87) PCT Pub. No.: WO2012/068493
PCT Pub. Date: May 24, 2012

(65) Prior Publication Data
US 2014/0005518 A1    Jan. 2, 2014

Related U.S. Application Data

(60) Provisional application No. 61/414,974, filed on Nov. 18, 2010.

(51) Int. Cl.
*A61B 5/04* (2006.01)
*A61B 5/00* (2006.01)

(52) U.S. Cl.
CPC ......... *A61B 5/04008* (2013.01); *A61B 5/04009* (2013.01); *A61B 5/6814* (2013.01); *A61B 5/721* (2013.01); *A61B 2562/0219* (2013.01)

(58) Field of Classification Search
CPC ................... A61B 2562/0219; A61B 5/04008; A61B 5/04009; A61B 5/6814; A61B 5/721
See application file for complete search history.

(56) References Cited

U.S. PATENT DOCUMENTS 4,913,152 A   4/1990   Ko et al.
4,951,674 A   8/1990   Zanakis et al.
(Continued)

FOREIGN PATENT DOCUMENTS

WO   2005/025416   3/2005

OTHER PUBLICATIONS

Cordova-Fraga et al, "Spatiotemporal evaluation of human colon motility using three-axis fluxgates and magnetic markers", Medical & Biological Engineering and Computing, 2005, vol. 43, pp. 712-715.*

(Continued)

*Primary Examiner* — Ruth S Smith
(74) *Attorney, Agent, or Firm* — Noah J. Hayward

(57) ABSTRACT

A magnetoencephalogram (MEG) system is provided for use with a head. The MEG system includes a shell, and three three-axis gradiometers and a computing portion. Each three-axis gradiometer detects a magnetic field vector from a magnetic dipole in the head and generates a respective detected signal based on the respective magnetic field vector. Each three-axis gradiometer is disposed at a respective position of the shell. The computing portion determines a location of the magnetic dipole based on the first detected signal, the second detected signal and the third detected signal.

16 Claims, 19 Drawing Sheets

(56) References Cited

U.S. PATENT DOCUMENTS

| | | | |
|---|---|---|---|
| 5,134,369 A * | 7/1992 | Lo et al. ............... | 324/245 |
| 5,657,756 A | 8/1997 | Vrba et al. | |
| 6,084,412 A | 7/2000 | Guo et al. | |
| 6,538,436 B1 | 3/2003 | Simola et al. | |
| 6,697,660 B1 | 2/2004 | Robinson | |
| 7,130,675 B2 | 10/2006 | Ewing et al. | |
| 7,197,352 B2 | 3/2007 | Gott et al. | |
| 7,729,740 B2 | 6/2010 | Kraus et al. | |
| 2002/0077537 A1 | 6/2002 | Avrin et al. | |
| 2005/0171421 A1 | 8/2005 | Eden et al. | |
| 2005/0234329 A1 * | 10/2005 | Kraus et al. ............ | 600/409 |
| 2006/0186881 A1 * | 8/2006 | Tilbrook ............... | 324/248 |
| 2007/0239059 A1 | 10/2007 | McIver | |

OTHER PUBLICATIONS

Ko et al., "A New Method for Magnetoencephalography," Johns Hopkins APL Technical Digest, vol. 9, No. 3, pp. 254-258 (1988).

Knappe et al., "Cross-validation of microfabricated atomic magnetometers with superconducting quantum interference devices for biomagnetic applications," Applied Physics Letters, 97, 133703, pp. 1-3 (Sep. 28, 2010).

Hansen et al., "Adaptive Noise Cancellation in Neuromagnetic Measurement Systems," Il Nuovo Cimento, vol. 2D, N. 2, pp. 203-213 (1983).

Ko et al., "Bioelectromagnetic Signal Processing," Biomedical Research, Development, and Engineering, The Johns Hopkins University Applied Physics Laboratory, pp. 33-35 (Oct. 1982).

Kotani et al., "A whole-head SQUID system for detecting vector components," Applied Superconductivity, vol. 5, No. 7-12, pp. 399-403 (Jul. 12, 1997).

Kobayashi et al., "Estimation of multiple sources using a three-dimensional vector measurement of a magnetoencephalogram," Journal of Applied Physics, vol. 83, No. 11, pp. 6462-6464 (Jun. 1, 1998).

* cited by examiner

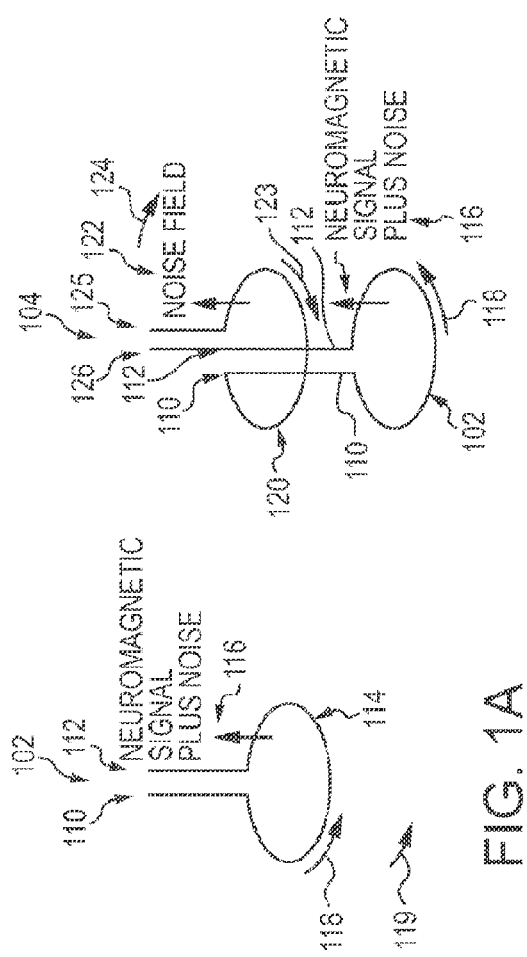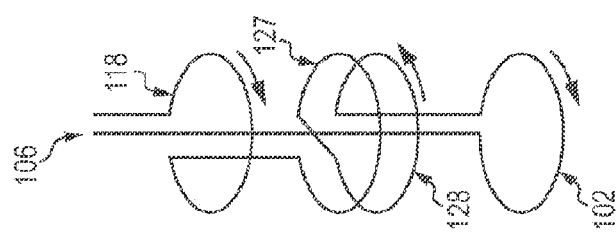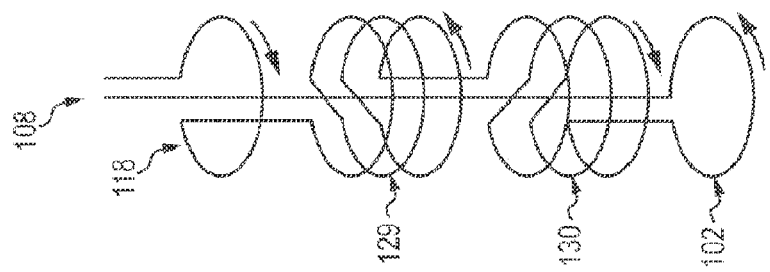

MAGNETOENCEPHALOGRAPHY SYSTEM AND METHOD FOR 3D LOCALIZATION AND TRACKING OF ELECTRICAL ACTIVITY IN BRAIN

The present application claims priority to and the benefit of U.S. Provisional Application No. 61/414,974 filed Nov. 18, 2010, the entire disclosure of which is incorporated herein by reference.

TECHNICAL FIELD

The present invention relates to portable magnetoencephalogram systems.

BACKGROUND ART

Magnetoencephalogram (MEG) techniques passively measure the magnetic fields emanating from neuronal sources in the brain. The MEG is the magnetic analogue of the electroencephalogram (EEG), which is a measure of potential differences about the brain caused by the electric fields emanating from neuronal sources within the brain. MEG and EEG signals originate from sources that can be modeled by current dipoles. For example, a hypothetical dendrite of dipole moment Q immersed in the electrically conducting brain is considered. The current dipole causes volume currents to flow in the brain and surrounding tissue, resulting in potential differences at the scalp. Those potentials are the signals measured by the EEG. A magnetic field, B, associated with the current dipole also is generated. This neuromagnetic field, which is measured by the MEG, has a field-spatial pattern giving contours of constant field (plus contours for B exiting, minus contours for B entering). The magnitude of the field diminishes as the contour radius increases.

The MEG has theoretical advantages over the EEG. A magnetic field noted as a vector B gives directional information about the source orientation. The neuromagnetic field B is not distorted by the brain, since the brain has the same permeability as air. The MEG is an absolute measure of source strength, not measured with respect to a reference, as is the EEG. The MEG is not affected by bad electrode contact or tissue artifacts, as is the EEG. The MEG does not need to touch the head, as does, the EEG.

The MEG has led to several investigations for locating the neuronal sources of magnetic signals emanating from the Brain under normal or pathological conditions. Neuromagnetic signals seen under normal conditions might be evoked responses from visual, auditory, somatic, or other stimuli. Normal brain rhythms (e.g., alpha and beta) are also seen. Neuromagnetic signals observed under pathological conditions might be associated with epilepsy4 or some other disease. The MEG shows potential for non-invasively localizing some sources of epilepsy located deep in the brain. At present, such sources are often localized by using EEG electrodes penetrating the brain. The MEG also shows potential for straightforward functional imaging of brain activity in mind-brain investigations. For example, psycho-physiological tests have shown that the MEG can measure brain activity during motor action and also in anticipation of motor action and in the absence of motor action. Such a dynamic real-time imaging response is not readily attainable by expensive positron emission tomography or magnetic resonance imaging systems.

FIGS. 1A-B illustrate example loops used in conventional single-axis gradiometer of conventional MEG systems.

In one example, a loop receives a neuromagnetic signal and noise. The loop converts received neuromagnetic signal plus noise to an electrical representation. This will be described with reference to FIG. 1A.

FIG. 1A is an illustration for a example conventional loop 102.

Loop 102 includes an entry portion 110, an exit portion 112 and a loop portion 114.

A detected magnetic field 116 passes through loop 102 and an electrical current 118 is generated. Electrical current 118 travels in the direction of an arrow 119. The amount of current generated is associated with an the amount of magnetic field received for detected magnetic field 116. Detected magnetic field 116 includes an amount of signal in additional to an amount of noise. In the case of use in a MEG system, the noise can be a factor of 10,000 times larger than the neuromagnetic signal. Generally, the noise originates from sources distant from the biological signal, and the noise field is spatially uniform. Loop 102 will detect a magnetic field along a single axis. When used in as a gradiometer, the gradiometer may detect a magnetic gradient along a single axis—the axis through the center of loop 102.

Methods have been developed to remove noise in a detected signal. For example, a first loop may be used to receive a neuromagnetic signal plus noise and another loop may be used to receive only noise. A combination may be used to remove the noise and generate a noise-free neuromagnetic signal. This will be further described with reference to FIG. 1B.

FIG. 1B is an illustration for another example conventional loop 104.

Loop 104 includes loop 102 and a loop 120.

Loop 120 detects a noise field 122. Loop 120, usually spaced several centimeters from loop 102, is used to measure the noise and not the neuromagnetic biological signal. Detected noise field 122 generates an electrical current 123. Electrical current 123 travels in the direction of an arrow 124. Loop 120 includes an input 125 and an output 126. The locations for the inputs and outputs are reversed for loop 102 as compared to loop 120. Electrical current 123 is in the opposite direction of electrical current 118 resulting in a subtraction of the currents. The subtraction in the currents results in noise being subtracted from the combination (of signal and noise) leaving a noise-free signal. This first-order difference subtracts out the spatially uniform noise field and reveals the signal. That difference can be accomplished by using one wire and winding the loops in opposing directions, as shown. This one-difference device is known as a single-differencing (or first-order) gradiometer. Similar to loop 102 discussed above, loop 104 will detect a magnetic field along a single axis. When used in as a gradiometer, the gradiometer may detect a magnetic gradient along a single axis—the axis through the center of loop 104.

In another example, a plurality of loops may be used to filter a non-spatially uniform noise field that varies linearly with distance. This will be further described with reference to FIG. 1C.

FIG. 1C is an illustration for a example conventional loop 106.

Loop 106 includes loop 102, loop 120, a loop 127 and a loop 128. Loop 127 and loop 128 are located between loop 102 and loop 120. Loop 127 and loop 128 form a difference of a difference (i.e., double difference) to cancel the noise. Such a device is called a double-differencing (or second-order) gradiometer. This configuration may be used for a non-spatially uniform noise field which varies linearly with distance. Similar to loop 102 discussed above, loop 106 will detect a magnetic field along a single axis. When used in as a gradiometer, the gradiometer may detect a magnetic gradient along a single axis—the axis through the center of loop 106.

FIG. 1D is an illustration for an example conventional loop 108.

Loop 108 includes loop 102, loop 120, a multi-turn loop 129 and a multi-turn loop 130.

Multi-turn loop 129 and multi-turn loop 130 are located between loop 102 and loop 120 with multi-turn loop 129 located adjacent to loop 102 and multi-turn loop 130 located adjacent to loop 120. Similar to loop 102 discussed above, loop 108 will detect a magnetic field along a single axis. When used in as a gradiometer, the gradiometer may detect a magnetic gradient along a single axis—the axis through the center of loop 108.

For conventional versions of this configuration, gradiometer magnetometers can have multi-turn loops immersed in a cryogenic fluid (e.g., liquid helium) to allow the loops to become superconducting. Superconducting loops are connected to a superconducting quantum interference device (SQUID), which is usually another wire loop with a Josephson tunneling junction used to detect the current flowing in the pick-up loop. The Josephson effect is the phenomenon of super current (i.e. a current that flows indefinitely long without any voltage applied) across to superconductors coupled by a weak link.

The pickup loop may be used in an MEG system, wherein liquid helium is used for cooling components. This will be described in greater detail with reference to FIG. 2A.

FIG. 2A is an illustration for a conventional MEG system having a conventional gradiometer 200 using the second-differencing pickup loop 106 as described with reference to FIG. 1C.

Conventional second-differencing gradiometer 200 includes loop 106, a SQUID 202, a liquid helium portion 204 and a housing 206.

SQUID 202 is used to measure weak magnetic fields using Josephson junction devices. A Josephson junction device relies on the Josephson phenomenon of a direct current crossing from the insulator in the absence of any external electromagnetic field, owing to tunneling. This DC Josephson current is proportional to the sine of the phase difference across the insulator. Liquid helium portion 204 is used to cool loop 106 and SQUID 202. Housing 206 is used for enclosing loop 106, SQUID 202 and liquid helium portion 204.

A single-field point measurement is made with the Second-Differencing Gradiometer (SSDG) at one station. As discussed above, SQUID 202 will detect a magnetic field along a single axis—the axis through the center of loop 106. To locate a single magnetic field, based on a motion of a magnetic dipole within the head, SQUID 202 will need to detect magnetic fields along many axes. Therefore, conventions MEG systems have as many as 100 gradiometer channels statically positioned about the head. The results from the as many as 100 measurements are then used in signal processing such as a Radon transform. An inverse the Radon transform is then used reconstruct an original magnetic field map of the head to deduce a location of a motion of a magnetic dipole within the head.

The MEG measurement is difficult. Non-limiting examples of background magnetic noise competing with neuromagnetic signals includes geomagnetic, geologic, urban, seismic, biological and sensor. Although gradiometric implementations can reduce the effects of some noise sources, the best MEG measurements also require the use of a magnetically shielded room, seismic isolation, auxiliary sensors and adaptive signal processing for further reduction of noise.

Conventional gradiometer 200 has issues with safety and volatility as super-cooled liquids such as Helium are used to provide cooling. Additionally, significant pressures are used for conventional gradiometer 200 requiring high levels of maintenance and monitoring. Furthermore, conventional gradiometer 200 are extremely large and complex and as a result are configured for stationary operation. Additionally, conventional gradiometer 200 consumes large amounts of energy and is very expensive to acquire and operate. Liquid Helium itself can be a scarce resource.

FIG. 2B is a picture of a conventional gradiometer system 210.

Gradiometer system 210 includes a plethora of loop 106 as described with reference to FIG. 2A.

FIG. 2B is a picture of a conventional gradiometer system demonstrating the size and complexity of a conventional gradiometer system.

As mentioned above, a MEG system may be used to map magnetic field contours on the head of a person. This will be further described with reference to FIGS. 3A-3D.

FIGS. 3A-D illustrate magnetic field contours derived with conventional systems.

FIG. 3A illustrates the magnetic field map over which an SSDG performs measurements. In the figure, a head 302 has an actual magnetic field contour map 304.

FIG. 3B illustrates the magnetic field data as measured for the magnetic field map as described with reference to FIG. 3A.

As shown in FIG. 3B, a magnetic field portion 306 is received via conventional second-differencing gradiometer 200, as described with reference to FIG. 2. Here, a first signal 308 and a second signal 310 are detected.

FIG. 3C illustrates the magnetic field data as measured for the magnetic field map at 1 second per position. In this example, four hours are needed to complete the measurement sequence. Here, first signal 308 and second signal 310 lead to subtle changes in the contour map as illustrated by a change 312.

FIG. 3D illustrates the magnetic field data as measured for the magnetic field map at 1 second per position with four hours needed to complete the measurement sequence.

First signal 308 and second signal 310 lead to subtle changed in contour map as illustrated by a change 314.

A contour map is drawn from the data, and sometimes, depending on the algorithm used, the dipole location is found along a line drawn to connect the positive peak contour with the negative peak contour. Generally, these simultaneous measurements are averaged over several seconds that cannot resolve the electrical track of the current dipoles as they progress through the brain to the region of the brain where the electrical activity is climaxed (e.g., cortex, hippocampus).

FIG. 4A illustrates a chart 400 for in vitro measurements performed using a conventional SSDG and spherical container filled with saline solution.

Chart 400 includes an x-axis 402 with units of degrees and a y-axis 404 representing magnetic field with normalized units.

The SSDG measures the magnetic field at different angular positions around oscillating current dipoles located 0.5, 1.5, 2.5, and 3.5 cm away from the center of a sphere (not shown) filled with saline solution. In one example, the sphere may be a 500-ml spherical flask.

A triangle dotted line 406 represents an oscillating current dipole located 1.0 cm away from the center of the container. A circle dotted line 408 represents an oscillating current dipole located 1.5 cm away from the center of the container. A heart dotted line 410 represents an oscillating current dipole located 2.5 cm away from the center of the container. A box dotted line 412 represents an oscillating current dipole located 3.5 cm away from the center of the container.

Triangle dotted line 406 initiates at an approximate y-axis value of 0.4 at an x-axis value of 0 degrees and increases monotonically until it reaches approximately a y-axis value of 3.5 and an approximate x-axis value of 70 degrees. Triangle dotted line 406 decreases monotonically from approximate y-axis value of 3.5 and an approximate x-value of 70 degrees until it reaches an approximate y-axis value of 2.5 and an x-axis value of 120 degrees.

Circle dotted line 408 initiates at an approximate y-axis value of 0.2 at an x-axis value of 0 degrees and increases monotonically until it reaches approximately a y-axis value of 3.4 and an x-axis value of 62 degrees. Circle dotted line 408 decreases monotonically from approximate y-axis value of 3.4 and an approximate x-axis value of 62 degrees until it reaches an approximate y-axis value of 1.7 and an x-axis value of 120 degrees.

Heart dotted line 410 initiates at an approximate y-axis value of 0.4 at an x-axis value of 0 degrees and increases monotonically until it reaches approximately a y-axis value of 3.4 and an x-axis value of 40 degrees. Heart dotted line 410 decreases monotonically from approximate y-axis value of 3.4 and an approximate x-axis value of 40 degrees until it reaches an approximate y-axis value of 1.1 and an x-axis value of 120 degrees.

Box dotted line 412 initiates at an approximate y-axis value of 0.1 at an x-axis value of 0 degrees and increases monotonically until it reaches approximately a y-axis value of 3.4 at an x-axis value of 33 degrees. Box dotted line 412 decreases monotonically from approximate y-axis value of 3.4 and an approximate x-axis value of 33 degrees until it reaches an approximate y-axis value of 0.6 and an x-axis value of 120 degrees.

The measurements show well-defined peaks that fit well with theory, provided the signal to noise ratio is large enough. Further, in this example, the container is spherical, thus the measurements are based on a somewhat symmetrical body. However, a human head is not spherical. To emulate a human head, a non-spherical shape should be used.

FIG. 4B illustrates a chart for measurements similar to FIG. 4A, however in FIG. 4B, the measurements were performed using a conventional SSDG and non-spherical container filled with saline solution. In particular, FIG. 4B illustrates the empirical results of similar measurements as FIG. 4A on oscillating current dipoles located 0.5, 1.0, 1.5, 2.5, and 3.5 cm away from the center of a non-spherical, teardrop-shaped reservoir filled with saline solution.

A diamond dotted line 414 represents an oscillating current dipole located 0.5 cm away from the center of the container.

Triangle dotted line 406 initiates at an approximate y-axis value of 0.3 at an x-axis value of 0 degrees and increases until it reaches an approximate y-axis value of 3.5 and an x-axis value of 120 degrees.

Circle dotted line 408 initiates at an approximate y-axis value of 0.3 at an x-axis value of 0 degrees and increases until it reaches an approximate y-axis value of 3.5 and an approximate x-axis value of 55 degrees. Circle dotted line 408 decreases from an approximate y-axis value of 3.5 and an approximate x-axis value of 55 degrees until it reaches an approximate y-axis value of 2.5 at an x-axis value of 120 degrees.

Heart dotted line 410 initiates at an approximate y-axis value of 0.3 at an x-axis value of 0 degrees and increases until it reaches approximately a y-axis value of 3.5 and an x-axis value of 40 degrees. Heart dotted line 410 decreases monotonically from an approximate y-axis value of 3.5 and an x-axis value of 40 degrees until it reaches an approximate y-axis value of 1.4 and an x-axis value of 120 degrees.

Box dotted line 412 initiates at an approximate y-axis value of 0.1 at an x-axis value of 0 degrees and increases monotonically until it reaches approximately a y-axis value of 3.5 and an x-axis value of 33 degrees. Box dotted line 412 decreases monotonically from approximate y-axis value of 3.5 and an x-axis value of 33 degrees until it reaches an approximate y-axis value of 0.7 and an x-axis value of 120 degrees.

Diamond dotted line 414 initiates at an approximate y-axis value of 0.2 at an x-axis value of 0 degrees and increases until it reaches a y-axis value of approximately 3.2 at an x-axis value of 120 degrees.

There is virtually no peak in the magnetic field pattern for in depth sources, and localization using the spherical theory is not possible. Investigators often fail to quantify the signal to noise ratio, laboratory noise, and the dependence of their localization on the number of measurement points and the choice of localization algorithm.

FIG. 4B illustrates a chart for measurements similar to FIG. 4A performed using a conventional SSDG and non-spherical container filled with saline solution where theory and practice may diverge.

FIG. 5 illustrates a chart 500 for Monte Carlo simulations of 10,000 trials of the localization performance amidst laboratory Gaussian noise using a conventional SSDG. Monte Carlo methods are a class of computational algorithms that rely on repeated random sampling to compute their results. These methods are most suited to calculation by computer and tend to be used when it is infeasible to compute an exact result with a deterministic algorithm.

The probability of localization measurement error for a dipole in a sphere with radius of 10 cm is described in terms of the signal to noise ration of the measurement. The dipole is positioned 4 cm from the sphere center.

Chart 500 includes an x-axis 502 representing a measurement error in millimeters and a y-axis 504 representing cumulative probability with units of normalized percent. A line 506 represents a signal to noise ratio of 10 dB. A line 508 represents a signal to noise ratio of 15 dB. A line 510 represents a signal to noise ratio of 20 dB. A line 512 represents a signal to noise ratio of 25 dB. The probability for error increases as the dipole is positioned closer to the sphere center.

The probability of reduced localization error is highly dependent on the signal to noise ratio. In simple MEG systems with a single channel, moving SSDG MEG devices from station to station causes three major problems. First, as a result of their extreme sensitivity and vector measurement potential, they can vibrate and give false signals resulting from their motion in the earth's static magnetic field. At the various measurement stations, the experimental vibration spectrum is different. Second, MEG devices are cryogenically cooled with liquid helium (i.e., they are superconducting magnetometers). Movement of those sensors from station to station around the head to generate contour maps causes inaccuracies in calibration due to the tilt and changes in helium levels. Third, at the new station or measurement point, the balance between the static magnetic field and internal magnetic trim tabs changes, creating potential calibration error.

FIG. 5 illustrates a chart for Monte Carlo simulations of 10,000 trials of the localization performance amidst laboratory Gaussian noise using a conventional SSDG where the probability for error increases as the dipole is positioned closer to the sphere center.

What is needed is a portable system and method for performing MEG.

BRIEF DISCLOSURE OF INVENTION

The present invention provides is a system and method for a portable MEG system.

In accordance with an aspect of the present invention, a MEG system is provided for use with a head. The MEG system includes a shell, and three three-axis gradiometers and a computing portion. The shell has an outer surface and an inner surface, wherein the inner surface is shaped to surround the head. The first three-axis gradiometer can detect a first magnetic field vector from a magnetic dipole in the head and can generate a first detected signal based on the first magnetic field vector. The first three-axis gradiometer is disposed at a first position of said inner surface. The second three-axis gradiometer can detect a second magnetic field vector from the magnetic dipole in the head and can generate a second detected signal based on the second magnetic field vector. The second three-axis gradiometer is disposed at a second position of said inner surface. The third three-axis gradiometer can detect a third magnetic field vector from the magnetic dipole in the head and can generate a third detected signal based on the third magnetic field vector. The third three-axis gradiometer is disposed at a third position of said inner surface. The computing portion can determine a location of the magnetic dipole based on the first detected signal, the second detected signal and the third detected signal.

Additional advantages and novel features of the invention are set forth in part in the description which follows, and in part will become apparent to those skilled in the art upon examination of the following or may be learned by practice of the invention. The advantages of the invention may be realized and attained by means of the instrumentalities and combinations particularly pointed out in the appended claims.

BRIEF DESCRIPTION OF DRAWINGS

The accompanying drawings, which are incorporated in and form a part of the specification, illustrate an exemplary embodiment of the present invention and, together with the description, serve to explain the principles of the invention. In the drawings:

FIGS. 1A-D illustrate an example pickup loop;

DETAILED DISCLOSURE OF INVENTION/MODES FOR CARRYING OUT THE INVENTION & INDUSTRIAL APPLICABILITY

The present invention provides a system and method for a portable MEG system, operating at room temperature, is comprised of a high magnetic permeability shell or helmet containing magnetic sensors that fits over and around the head to sense the magnetic fields from electrical activity in the brain. The magnetic sensor signals are transmitted to a computer that calculates the location and time evolution track of the electrical currents of brain activity. The brain activity may be part of normal brain activity without external stimuli; response to external stimuli such as Visual Evoked Response (VER), Auditory Evoked Response (AER), or Somatosensory Evoked Response (SER); or a result of an electrical discharge from pathological foci due to brain dysfunction. Further, a MEG system in accordance with aspects of the present invention enable three dimensional tracking of a dipole within a head.

Figure 2A:
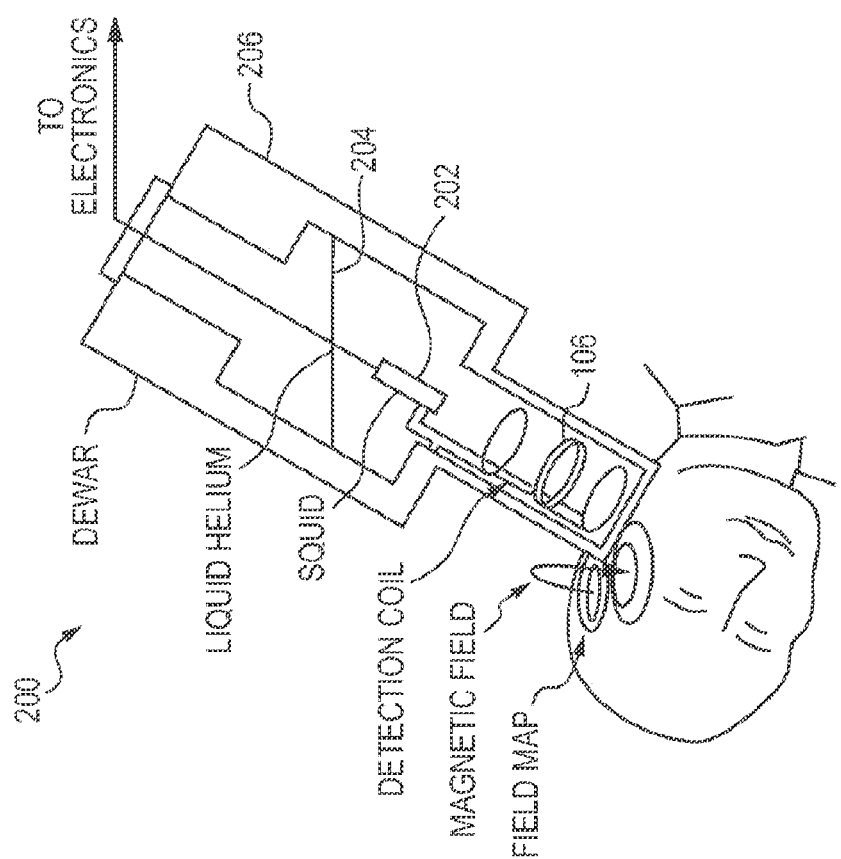
FIG. 2A is an illustration for a conventional second-differencing gradiometer using the second-differencing pickup loop as described with reference to FIG. 1C.
Figure 2B:
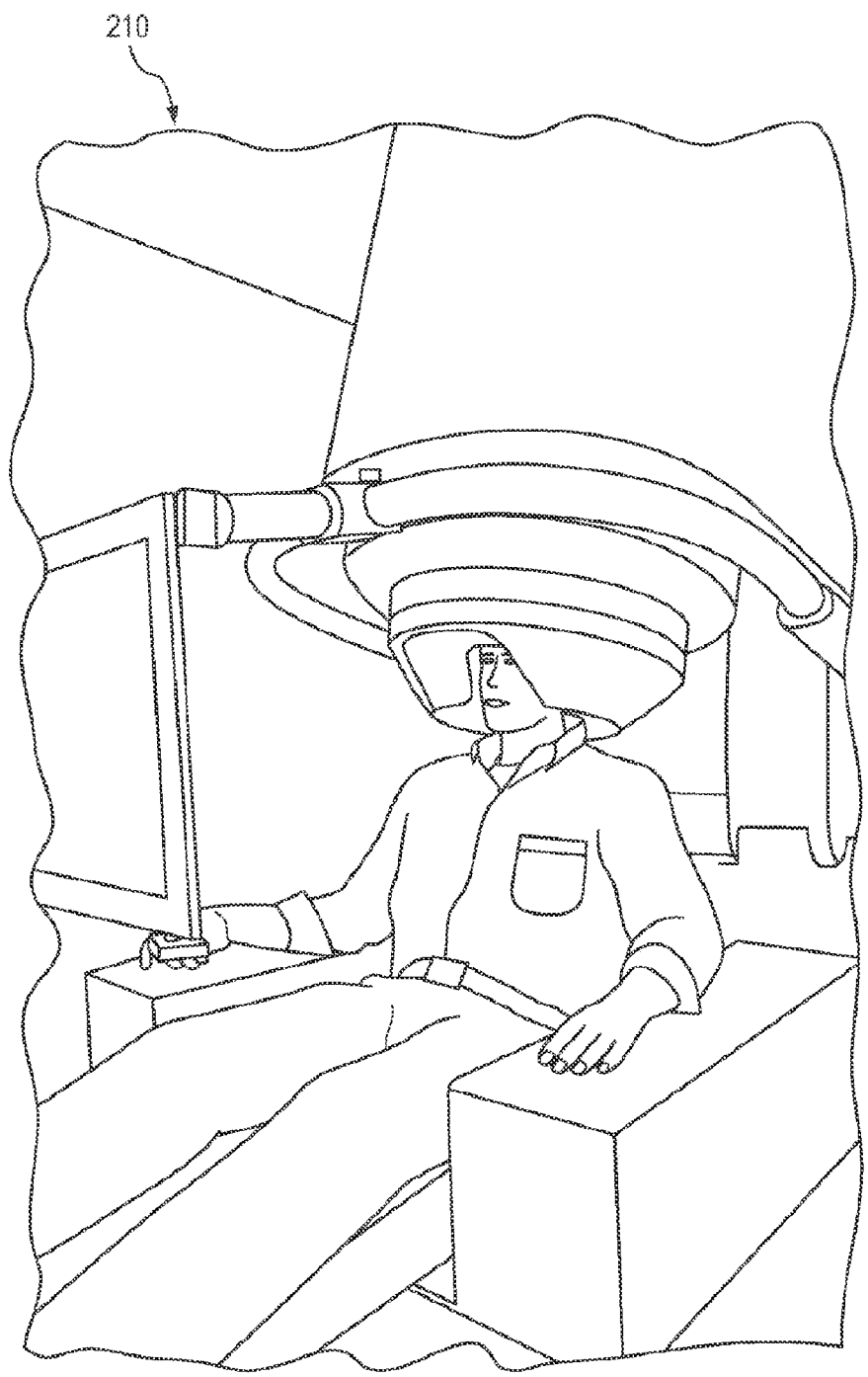
FIG. 2B is a picture of a conventional gradiometer system.
Figure 3D:
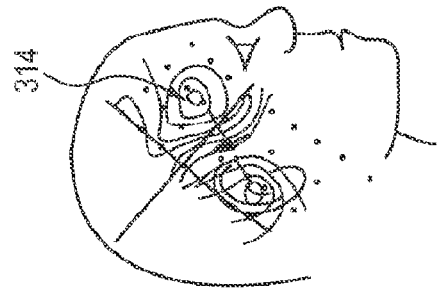
FIGS. 3A-D illustrate magnetic field contours derived with conventional systems.
Figure 3C:
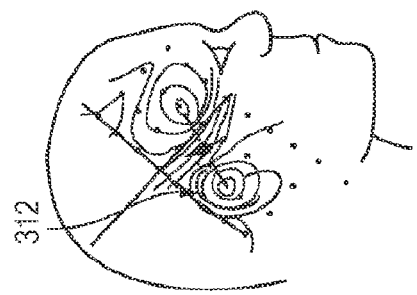
Figure 3B:
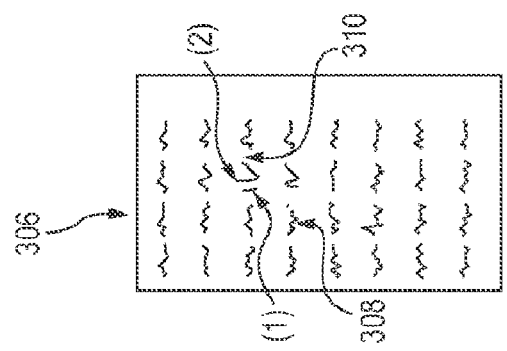
Figure 3A:
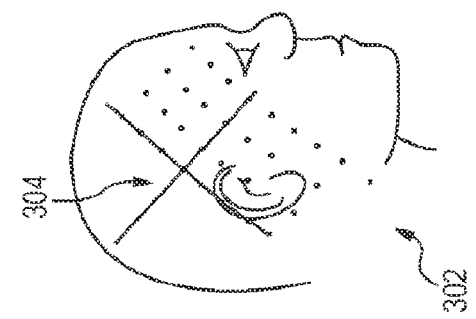
Figure 4A:
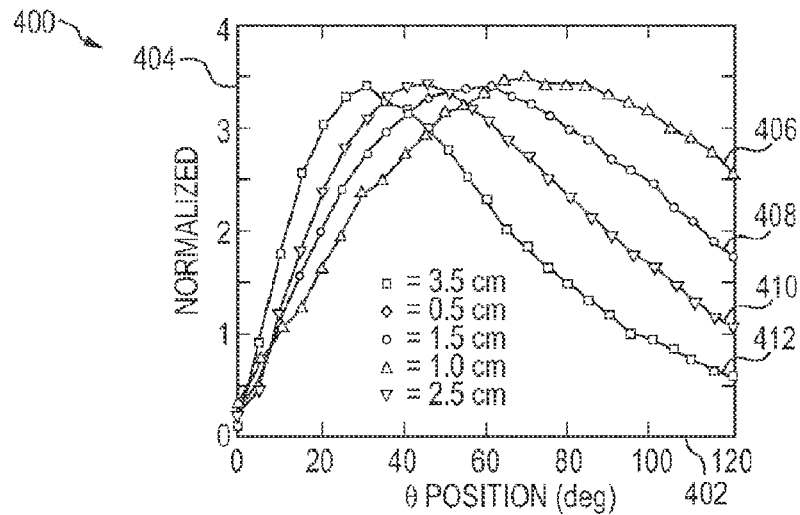
FIG. 4A illustrates a chart for in vitro measurements performed using a conventional SSDG and spherical container filled with saline solution.
Figure 4B:
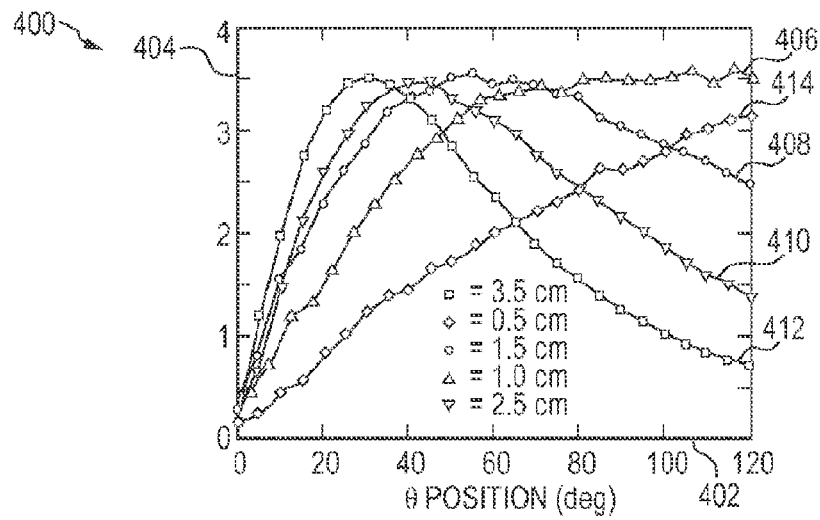
FIG. 4B illustrates a chart for measurements similar to FIG. 4A performed using a conventional SSDG and non-spherical container filled with saline solution.
Figure 5:
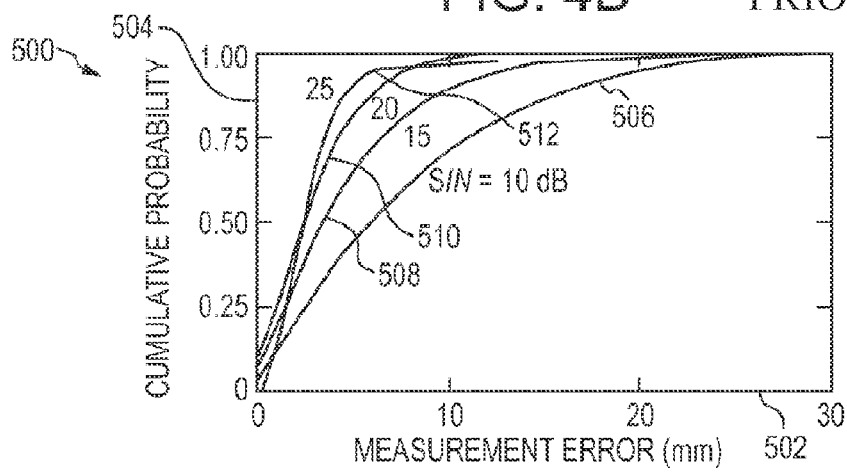
FIG. 5 illustrates a chart for Monte Carlo simulations of 10,000 trials of the localization performance amidst laboratory Gaussian noise using a conventional SSDG.

Contrary to the conventional MEG systems discussed above with reference to FIGS. 1-2B, a MEG system in accordance with aspects of the present invention uses three-axis gradiometers. In an example embodiment, three three-axis gradiometers are positioned at three locations about a head. Each of the three three-axis gradiometers is able to detect and spatially track three respective magnetic field vectors resulting from a magnetic dipole within the head. Signals from the three three-axis gradiometers may be used to accurately determine a location of the dipoles within the head. Accordingly, in contrast with a conventional MEG system using a single-axis gradiometer that may take 100 or more simultaneous measurements around the head in an attempt to locate electrical-magnetic signals in a head, a MEG system using three three-axis gradiometers in accordance with aspects of the present invention may take three measurements (at a single time) to locate and track motion of a dipole in a head. The MEG system using three three-axis gradiometers in accordance with aspects of the present invention does not need to rely on reconstruction based on analytical deductions from head models.

As for localization and tracking, the three-axis gradiometers, any type of known magnetometer may be used, so long as the magnetometer(s) are arranged to detect the three gradiometers axes of magnetic fields.

In accordance with another aspect of the present invention, additional sensors may be used in conjunction with the three-axis gradiometers in order to cancel noise. For example, accelerometers may be placed on the person to detect movement, e.g., movement of the arm to scratch an itch during the MEG measurements. Signals from the accelerometer may be used to subtract noise associated with the arm movement.

In accordance with another aspect of the present invention, additional sensors may be used in conjunction with the three-axis gradiometers in order to verify associations of magnetic dipoles within the brain. For example, photosensors may be used to detect a flash of light, to which a person is subjected. The flash of light my incite brain activity, which will generate motions of magnetic dipole within the brain. Signals from the photosensors may be used to verify brain activity associated with the effect of bright light on the person.

In accordance with another aspect of the present invention, a MEG system using three three-axis gradiometers may be used to diagnose and or predict dysfunctional brain activity based on known electrical rhythms of the brain. For example, known Beta, Alpha Theta and Delta brain rhythms are detectable with conventional electroencephalogram EEG. However, these known rhythms may additionally be monitored with a MEG system using three three-axis gradiometers in accordance with aspects of the present invention.

Aspects of the present invention will now be described in detail with reference to FIGS. 6-30.

In an example MEG system in accordance with aspects of the present invention, a stimulus and noise are received by a person. The magnetic dipoles associated with the stimulus and noise are then tracked within person's head. This will be described in greater detail with reference to FIG. 6.

Figure 6:
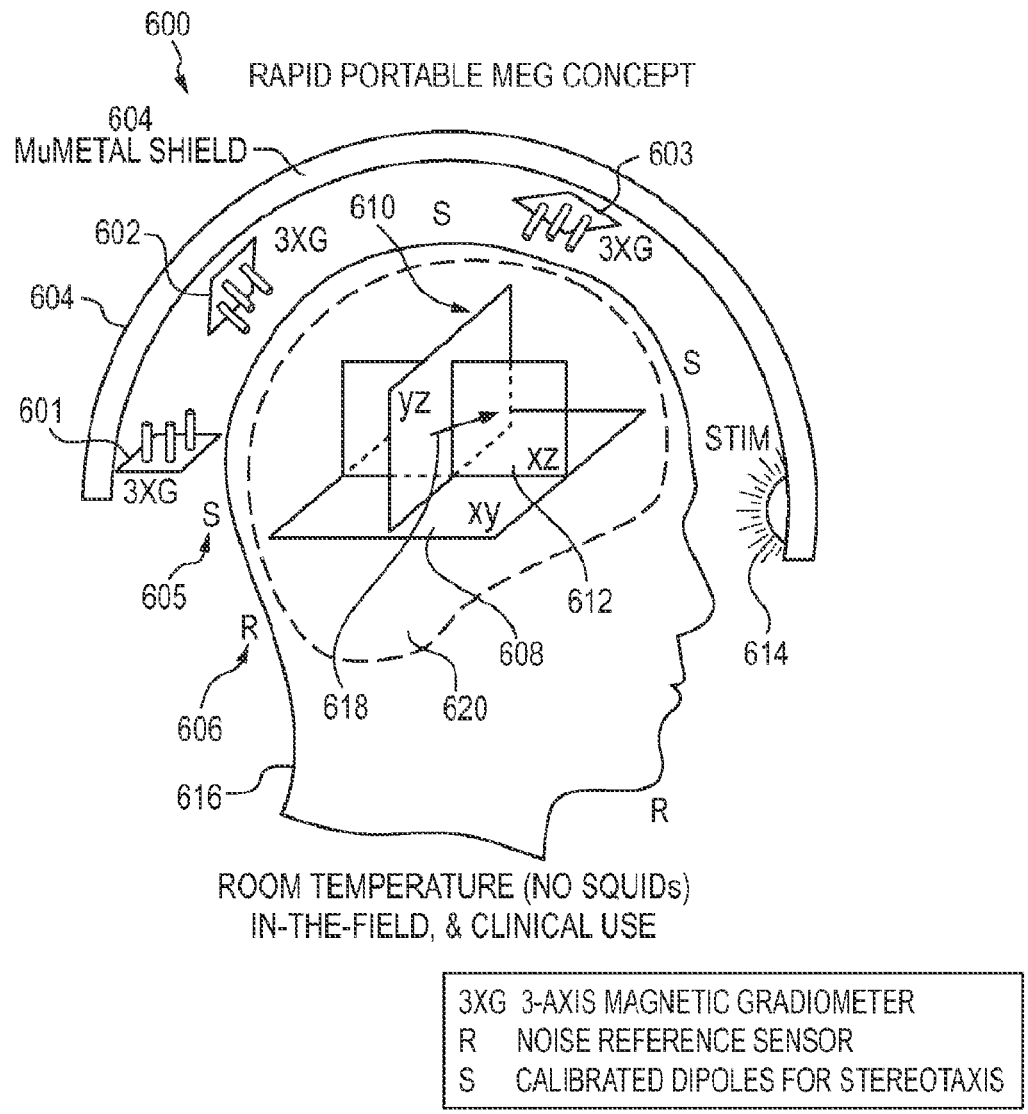
FIG. 6 is an illustration for an example MEG sensor portion, in accordance with an aspect of the present invention.

FIG. 6 is an illustration for an example MEG sensor portion 600, in accordance with an aspect of the present invention.

MEG sensor portion 600 includes a first three-axis magnetic gradiometer portion 601, a second three-axis magnetic gradiometer portion 602, a third three-axis magnetic gradiometer portion 603, a shield 604, a plurality of dipoles with a sampling noted as a magnetic dipole 605 and plurality of noises references with a sampling noted as a noise reference sensor 606.

First three-axis magnetic gradiometer portion 601 is oriented for receiving magnetic field information with respect to an x-y plane 608. Second three-axis magnetic gradiometer portion 602 is oriented for receiving magnetic field information with respect to a y-z plane 610. Third three-axis magnetic gradiometer portion 603 is oriented for receiving magnetic field information with respect to an x-z plane 612.

Shield 604 encompasses first three-axis magnetic gradiometer portion 601, second three-axis magnetic gradiometer portion 602, third three-axis magnetic gradiometer portion 603 and magnetic dipole 605.

Shield 604 shields the encompassed elements from external electrical and magnetic fields. In an example embodiment, shield 604 attenuates static and low-frequency magnetic fields. Shield 604 may include mu-metal, a non-limiting example of which includes a nickel-iron alloy.

First three-axis magnetic gradiometer portion 601, second three-axis magnetic gradiometer portion 602 and third three-axis magnetic gradiometer portion 603 detect and communicate information associated with magnetic fields.

In operation, s magnetic field associated with magnetic dipole 605 is received simultaneously by first three-axis magnetic gradiometer portion 601, second three-axis magnetic gradiometer portion 602 and third three-axis magnetic gradiometer portion 603. Information received for first three-axis magnetic gradiometer portion 601, second three-axis magnetic gradiometer portion 602 and third three-axis magnetic gradiometer portion 603 is processed for calibrating system associated with MEG sensor portion 600.

Magnetic noise, not associated with magnetic dipole 605, is received by a head 616. To account for other possible extraneous magnetic signals, not associated with magnetic dipole 605, a stimulus 614 is generated and applied to head 616. Stimulus 614 and magnetic noise is received by head 616 and converted to an electrical representation 618 of the received stimulus and noise. Electrical representation 618 travels from the person's extremities where the stimulus is applied to internal elements of head 616 such as a brain 620. As electrical representation 618 travels through head 616, first three-axis magnetic gradiometer portion 601 detects magnetic fields associated with electrical representation 618 with respect to x-y plane 608. Furthermore, second three-axis magnetic gradiometer portion 602 detects magnetic fields associated with electrical representation 618 with respect to y-z plane 610. Furthermore, third three-axis magnetic gradiometer portion 603 detects magnetic fields associated with electrical representation 618 with respect to x-z plane 612.

Furthermore, magnetic noise associated with noise reference sensor 606 is received and filtered for removal of the noise from electrical representation 618.

In order to track a dipole within a plane, in accordance with aspects of the present invention, three-dimensional gradient sensor is used. This will be described in greater detail with reference to FIGS. 7A-7B.

Figure 7A:
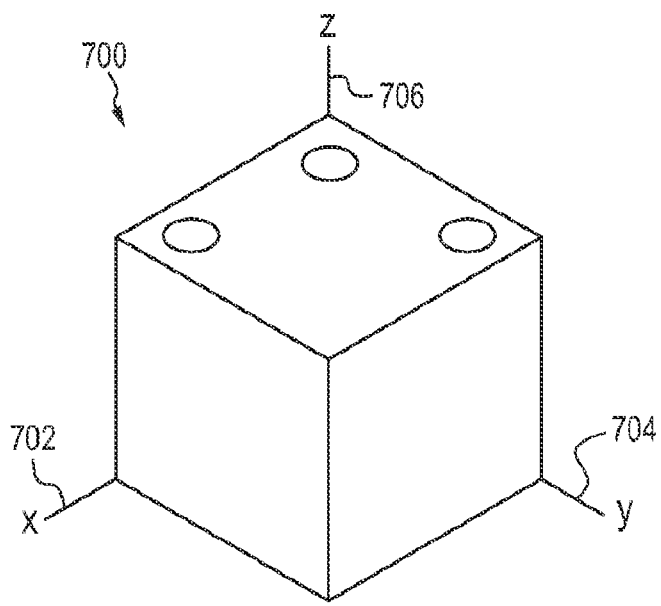
FIG. 7A illustrates sensor loop orientation for complete gradient sensor for three-dimensional tracking.

FIG. 7A illustrates sensor loop (i.e., sensor plane normal to the magnetic field) orientation for complete gradient sensor for three-dimensional tracking.

A chart 700 includes an x-axis 702 with dimensions of meters, a y-axis 704 with dimension of meters and a z-axis 706 with dimensions of meters.

It can be shown that a five axis gradiometer can yield a three-dimensional localization. It can also track a static, ferromagnetic dipole at ranges from tens to thousands of meters, depending on the dipole source strength and magnetometer sensitivity.

Figure 7B:
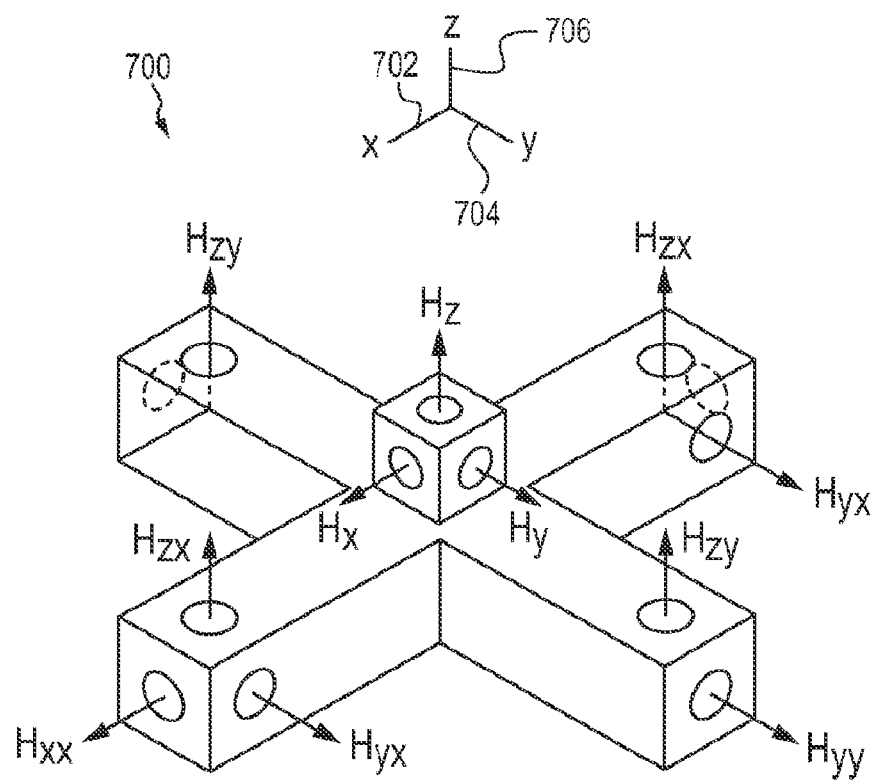
FIG. 7B illustrates sensor loop orientation for three-gradient version with x-y tracking, in accordance with an aspect of the present invention.

FIG. 7B illustrates sensor loop orientation for three-gradient version with x-y tracking, in accordance with an aspect of the present invention.

It can also be shown that a simpler three-axis device can provide two-dimensional localization and tracking. For example, returning to FIG. 6, first three-axis magnetic gradiometer portion 601 is able to provide two-dimensional localized tracking on x-y plane 608.

In accordance with aspects of the present invention, an MEG system may measure the magnetic field associated an electrical current and may communicate the measured information to a computing device. Furthermore, computing device may process the received information in order to image the motion of electrical current located within a plane. This will be described in greater detail with reference to FIG. 8.

Figure 8:
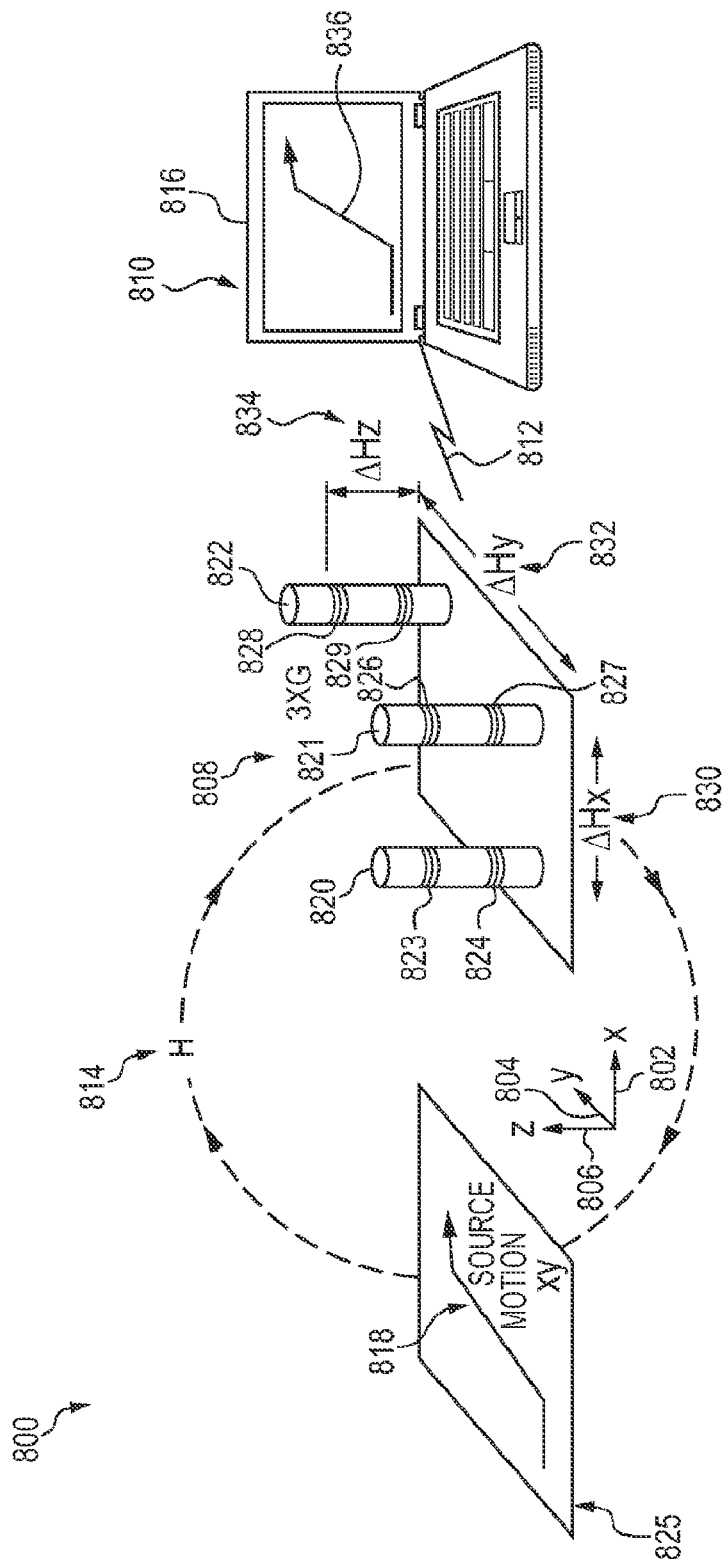
FIG. 8 is an illustration for an example MEG system, in accordance with an aspect of the present invention.

FIG. 8 is an illustration for an example MEG system 800, in accordance with an aspect of the present invention.

MEG system 800 is located in three-dimensional space with an x-axis 802, a y-axis 804 and a z-axis 806 with units of inches.

The MEG system 800 includes a three-axis magnetic gradiometer portion 808 and a computing device portion 810. In this example embodiment, three-axis magnetic gradiometer portion 808 operates in three dimensions. Computing device portion 810 may be any known computing device, non-limiting examples of which include a personal computer, a netbook computer, a notebook computer, a tablet device and a smartphone.

Computing device portion 810 receives information from three-axis magnetic gradiometer portion 808 via a communication channel 812. Three-axis magnetic gradiometer portion 808 detects and communicates information associated with a magnetic field 814. Computing device portion 810 receives and processes information from three-axis magnetic gradiometer portion 808 to present for viewing via a presentation portion 816.

Three-axis magnetic gradiometer portion 808 includes a detector portion 820, a detector portion 821 and a detector portion 822. Detector portion 820 includes a loop 823 and a loop 824. Detector portion 821 includes a loop 826 and a loop 827. Detector portion 822 includes a loop 828 and a loop 829. In an example embodiment, loops 823, 824, 826, 827, 828 and 829 may be configured as loop 102, 104, 106 or loop 108 as described with reference to FIG. 1.

Magnetic field 814 is created as a result of the motion of electrons associated with an electrical current 818, which may be a result of electrical activity in a brain.

In an example embodiment, the three sensors associated with three-axis magnetic gradiometer portion 808 provide the capability for two-dimensional localization and tracking. For this example, three-axis magnetic gradiometer portion 808 provides capability for measuring the z component of magnetic field 814 and for tracking the motion of electrical current 818 in an x-y plane 825.

Detector portion 820, detector portion 821 and detector portion 822 are oriented to measure the z component of the magnetic field. These sensors are positioned laterally along the x and y directions. Taking the difference between detector portion 820 and detector portion 821 gives gradient Equation (1)

$$\frac{H_1 - H_2}{\Delta x} = \frac{\Delta H_z}{\Delta x} = H_{zx}. \tag{1}$$

Taking the difference between detector portion 821 and detector portion 822 gives gradient Equation (2)

$$\frac{H_2 - H_3}{\Delta y} = \frac{\Delta H_z}{\Delta y} = H_{zy}. \tag{2}$$

The x and y locations of the dipole are given by Equation (3) and Equation (4)

$$x = \frac{-3H_z H_{zx}}{H_{zx}^2 + H_{zy}^2} \tag{3}$$

$$y = \frac{-3H_z H_{zy}}{H_{zx}^2 + H_{zy}^2}, \tag{4}$$

and the vertical magnetic-moment source strength, $M_z$, of the dipole is given by Equation (5)

$$M_z = -H_z(x^2 + y^2)^{1/2}. \tag{5}$$

The solutions to Equations 3 and 4 provide a location of a dipole in an x-y plane, e.g., x-y plane 608. Measurements from each of the three three-axis magnetic gradiometers provide input for Equations 3 and 4. Accordingly, by using three three-axis magnetic gradiometers, the location of a dipole in an x-y plane, in an x-z plane and a y-z plane may be easily determined.

For example, returning to FIG. 7, each three-axis magnetic gradiometer includes a magnetic detecting portion pointing in a z direction, which will measure a z component of a magnetic field. Now, with reference to FIG. 6, consider two of three-axis magnetic gradiometers separated in an x direction, e.g. first three-axis magnetic gradiometer portion 601 and second three-axis magnetic gradiometer portion 602. $H_z$ (of Equation 3) may be measured by each of one portion of first three-axis magnetic gradiometer portion 601 and one portion of second three-axis magnetic gradiometer portion 602. $H_{z1}$ as measured at the position of first three-axis magnetic gradiometer portion 601 may be subtracted from $H_{z2}$ as measured at the position of second three-axis magnetic gradiometer portion 602 to obtain the $H_{zx}$ gradient (of Equation 3). Similar measurements may be taken to calculate gradients in all axes. Implementations of Equations 1-5 with three-axis magnetic gradiometers will be described in greater detail below.

An x-magnetic difference 830 is calculated as the difference in the magnetic field as measured by detector portion 820 and detector portion 821. A y-magnetic difference 832 is calculated as the difference in the magnetic field as measured by detector portion 821 and detector portion 822. A z-magnetic difference 834 is calculated as the vertical distance between loop 828 and loop 829.

The x-magnetic difference 830 is used in conjunction with Equation (1) for determining $H_{zx}$ which is then used in Equation (3) to find the x location and is used in Equation (4) to find the y location. The y-magnetic difference 832 is used in conjunction with Equation (2) for determining $H_{zy}$, which is then used in Equation (3) to find the x location and is used in Equation (4) to find the y location.

By using three implementations of three-axis magnetic gradiometer portion 808 as described with reference to first three-axis magnetic gradiometer portion 601, second three-axis magnetic gradiometer portion 602 and third three-axis magnetic gradiometer portion 603 in FIG. 6 and then using Equations 1-5, the movement of a magnetic dipole may be tracked in a three dimensional volume. First three-axis magnetic gradiometer portion 601, second three-axis magnetic gradiometer portion 602 and third three-axis magnetic gradiometer portion 603 have two loops and an associated height difference, for example as illustrated by three-axis magnetic gradiometer portion 808, for tracking the movement of a magnetic dipole in the respective planes. Furthermore, the location information determined for the planes may then be used for tracking the movement of a magnetic dipole in a three-dimensional volume.

In operation, magnetic field 814 associated with the movement of electrical current 818 is received by three-axis magnetic gradiometer portion 808. Three-axis magnetic gradiometer portion 808 communicates information associated with magnetic field 814 to computing device portion 810 via communication channel 812. Computing device portion 810 receives and processes information received from three-axis magnetic gradiometer portion 808 in order to display a presentation 836 for viewing via presentation portion 816. For this example, presentation 836 is a replica for the movement of electrical current 818.

In accordance with aspects of the present invention, a three-gradient x-y tracking system may be provided, where a magnetic field is generated and a circuit receives and processes the magnetic field to provide x and y dimension location information. This will be described with reference to FIG. 9.

Figure 9:
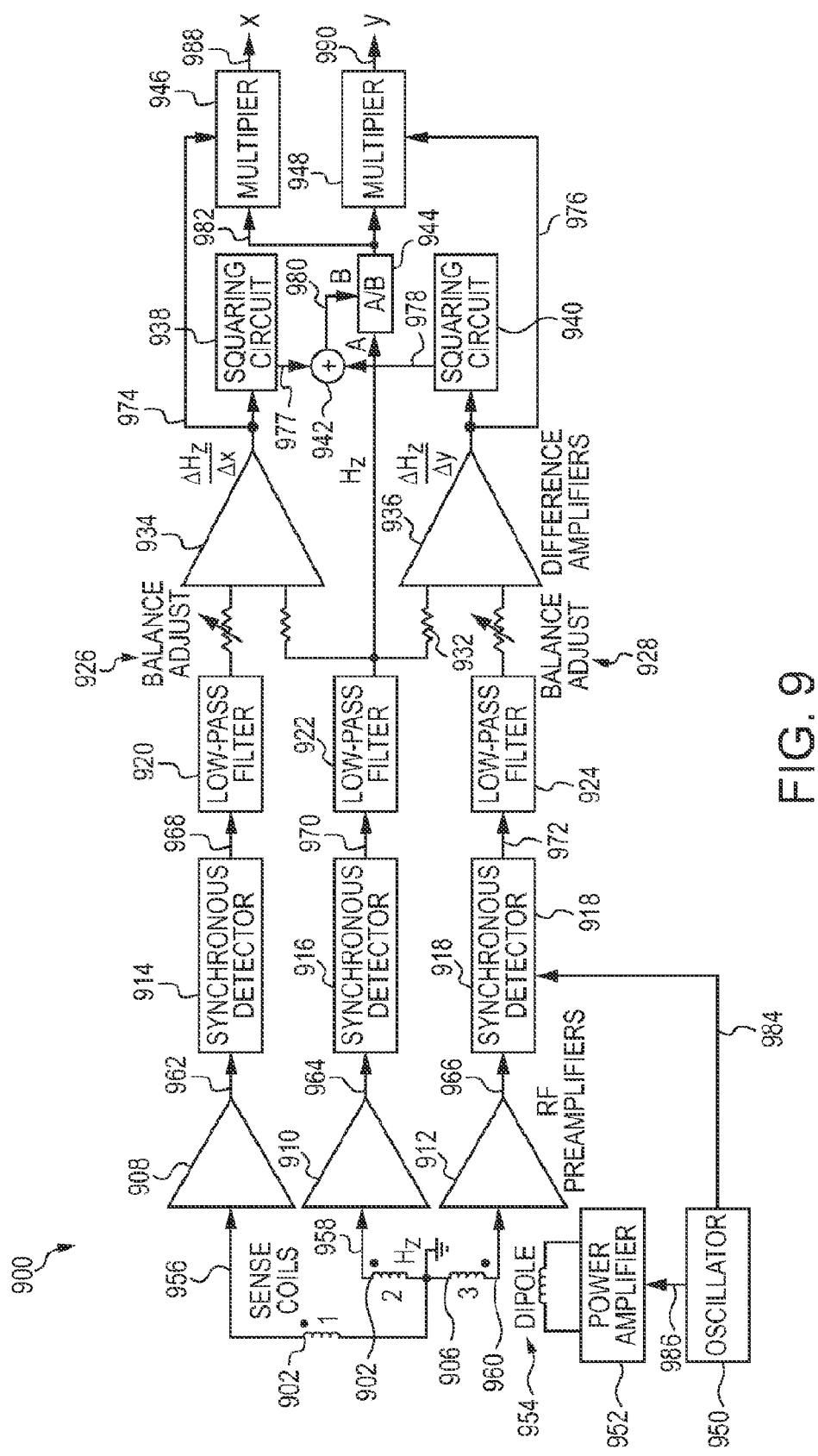
FIG. 9 illustrates a circuit diagram for a three-gradient x-y tracking system, in accordance with an aspect of the present invention.

FIG. 9 illustrates an example circuit diagram for a three-gradient x-y tracking system 900, in accordance with an aspect of the present invention.

Three-gradient x-y tracking system 900 includes a sense loop 902, a sense loop 904, a sense loop 906, an RF preamplifier 908, an RF preamplifier 910, an RF Preamplifier 912, a synchronous detector 914, a synchronous detector 916, a synchronous detector 918, a low-pass filter 920, a low-pass filter 922, a low-pass filter 924, a balance adjust 926, a balance adjust 928, a resistor 930, a resistor 932, a difference amplifier 934, a difference amplifier 936, a squaring circuit 938, a squaring circuit 940, a summation circuit 942, a divisor circuit 944, a multiplier 946, a multiplier 948, an oscillator 950, a power amplifier 952 and a dipole 954.

Sense loop 902, sense loop 904 and sense loop 906 detect magnetic fields. RF preamplifier 908, RF preamplifier 910 and RF preamplifier 912 amplify signals. Synchronous detector 914, synchronous detector 916 and synchronous detector 918 perform synchronous detection. Low-pass filter 920, low-pass filter 922 and low-pass filter 924 perform low-pass filtering.

Balance adjust 926 and balance adjust 928 provide balance adjustment. Resistor 930 and resistor 932 provide a path of resistance. Difference amplifier 934 and difference amplifier 936 provide difference amplification. Squaring circuit 938 and squaring circuit 940 provide a squaring function. Summation circuit 942 provides a sum of two input signals. Multiplier 946 and multiplier 948 provide a multiplication function.

Oscillator 950 provides a continuous sinusoidal signal. Power amplifier 952 provides amplification. Dipole 954 provides a magnetic field.

RF preamplifier 908 receives a signal 956 from a first leg of sense loop 902. RF preamplifier 910 receives a signal 958 from a first leg of sense loop 904. RF preamplifier 912 receives a signal 960 from a first leg of sense loop 906. Second leg of sense loop 902, second leg of sense loop 904 and second leg of sense loop 906 connect to ground.

Synchronous detector 914 receives a signal 962 from output of RF preamplifier 908. Synchronous detector 916 receives a signal 964 from output of RF preamplifier 910. Synchronous detector 918 receives a signal 966 from output of RF preamplifier 912. Low-pass filter 920 receives a signal 968 from output of synchronous detector 914. Low-pass filter 922 receives a signal 970 from output of synchronous detector 916. Low-pass filter 924 receives a signal 972 from output of synchronous detector 918.

A first leg of balance adjust 926 connects to output of low-pass filter 920. A first leg of balance adjust 928 connects to output of low-pass filter 924. A first leg of resistor 930 receives a signal 973 from output of low-pass filter 922. A first leg of resistor 932 receives signal 973 from output of low-pass filter 922.

Negative input of difference amplifier 934 connects to second leg of balance adjust 926. Positive input of difference amplifier 934 connects to second leg of resistor 930. Negative input of difference amplifier 936 connects to second leg of resistor 932. Positive input of difference amplifier 936 connects to second leg of balance adjust 928.

Squaring circuit 938 receives a signal 974 from output of difference amplifier 934. Squaring circuit 940 receives a signal 976 from output of difference amplifier 936. Summation circuit 942 receives a signal 977 from output of squaring circuit 938 and receives a signal 978 from output of squaring circuit 940. Divisor circuit 944 receives a signal 980 from output of summation circuit 942 and receives signal 973 from output of low-pass filter 922. Multiplier 946 receives a signal 982 from output of divisor circuit 944 and signal 974 from output of difference amplifier 934. Multiplier 948 receives signal 982 from output of divisor circuit 944 and signal 976 from output of difference amplifier 936.

Synchronous detector 918 receives a signal 984 from output of oscillator 950. Power amplifier 952 receives a signal 986 from output of oscillator 950. A first leg of dipole 954 connects to a first output of power amplifier 952 and a second leg of dipole 954 connects to a second output of power amplifier 952.

An x-dimension location is provided via a signal 988 received from output of multiplier 946.

A y-dimension location is provided via a signal 990 received from output of multiplier 948.

In operation, power amplifier 952 receives a signal from oscillator 950. Dipole 954 receives the amplified signal and generates a magnetic field. The magnetic field information is received by RF preamplifier 908, Rf preamplifier 910 and RF preamplifier 912 via sense loop 902, sense loop 904 and sense loop 906, respectively. Synchronous detector 914, synchronous detector 916 and synchronous detector 918 receive amplified magnetic field information from RF preamplifier 908, Rf preamplifier 910 and RF preamplifier 912, respectively and perform synchronous detection.

Low-pass filter 920, low-pass filter 922 and low-pass filter 924 receive synchronized magnetic field information from synchronous detector 914, synchronous detector 916 and synchronous detector 918, respectively and perform low-pass filtering. Difference amplifier 934 receives filtered synchronized magnetic field information to generate $\Delta H_z/\Delta x$. Difference amplifier 936 receives filtered synchronized magnetic field information to generate $\Delta H_z/\Delta y$.

Squaring circuit 938 performs a squaring operation of received gradient information (i.e. $\Delta H_z/\Delta x$). Squaring circuit 940 performs a squaring operation of received gradient information (i.e. $\Delta H_z/\Delta y$). Summation circuit 942 receives the squared gradient information and performs a summation. Divisor circuit 944 performs a division of the summed and squared gradients. Multiplier 946 receives the gradient information (i.e. $\Delta H_z/\Delta x$) and the summed/squared gradients and performs a multiplication. Multiplier 948 receives the gradient information (i.e. $\Delta H_z/\Delta y$) and the summed/squared gradients and performs a multiplication. The x-dimension information is provided via multiplier 946 and the y-dimension information is provided via multiplier 948.

The three-gradient x-y tracking system, in accordance with aspects of the present invention is able to not only detect a magnetic dipole, but track the motion of the magnetic dipole. This will be described with additional reference to FIGS. 10A-B.

Figure 10A:
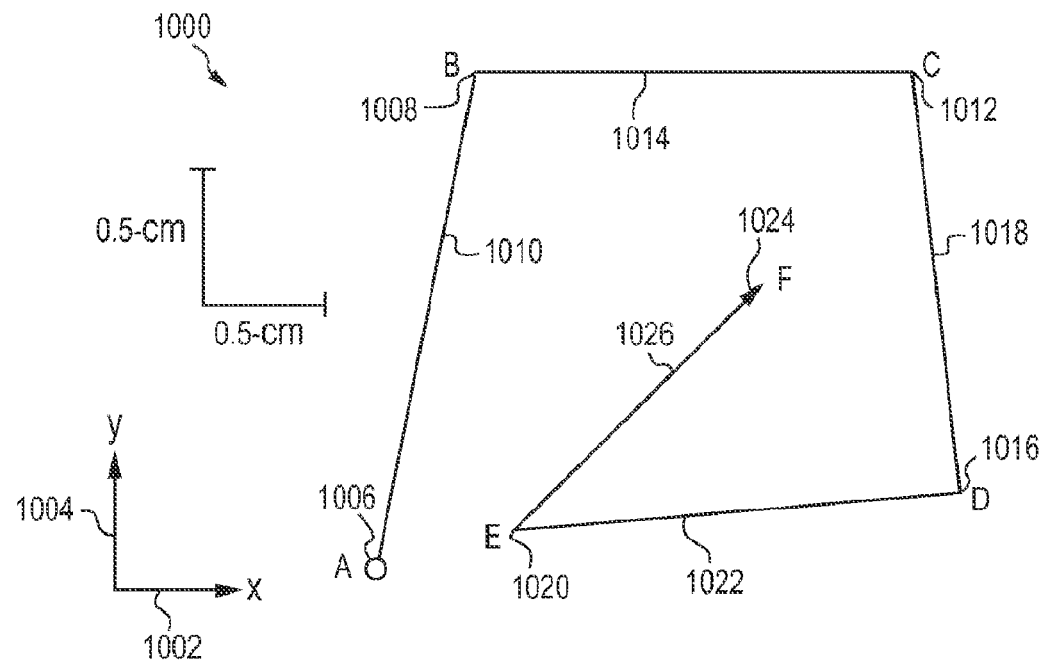
FIG. 10A presents an example graph illustrating a path of travel, in accordance with an aspect of the present invention.

FIG. 10A presents an example graph 1000 illustrating a path of travel associated with a magnetic dipole.

Graph 1000 includes an x-axis 1002 with dimensions of millimeters and a y-axis 1004 with dimensions of millimeters.

In this example, a magnetic dipole first travels up and to the right from a point 1006 to a point 1008 via a segment 1010. The magnetic dipole then travels in the positive x-direction from point 1008 to a point 1012 via a path 1014. The magnetic dipole then travels down and to the right from point 1012 to a point 1016 via a path 1018. The magnetic dipole then travels left and slightly down from point 1016 to a point 1020 via a path 1022. Finally, the magnetic dipole travels up and to the right from point 1020 to a point 1024 via a path 1026.

Figure 10B:
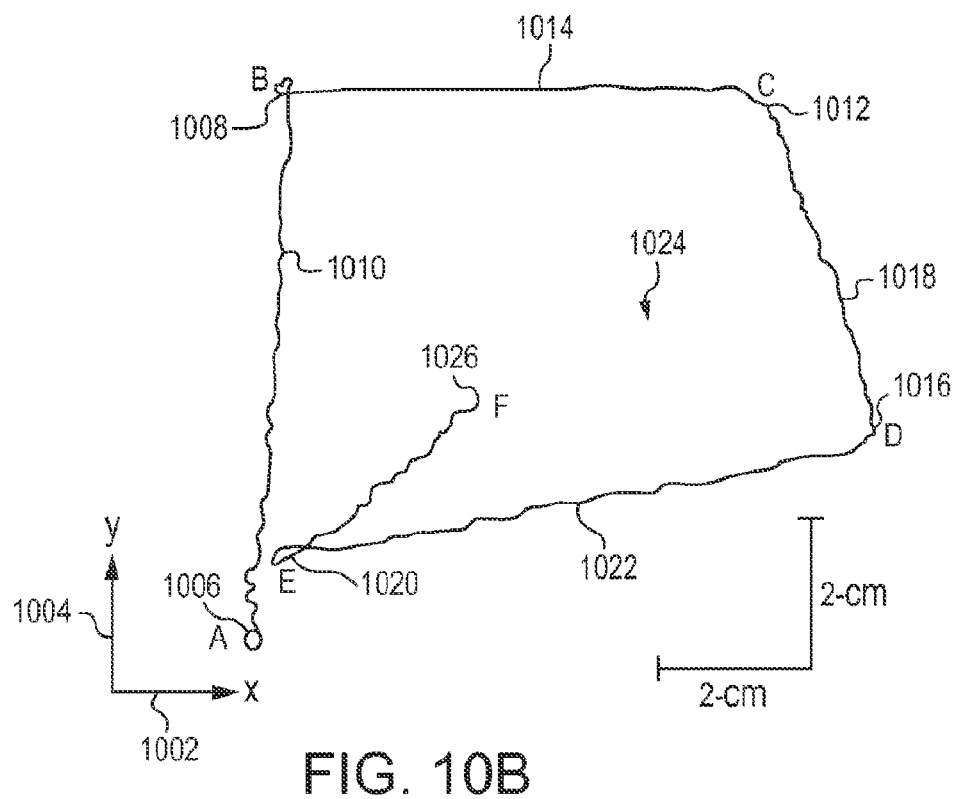
FIG. 10B presents example graph illustrating a path of travel using a three-gradient x-y tracking system, in accordance with an aspect of the present invention.

FIG. 10B presents example graph 1000 illustrating the detected path of travel for the actual magnetic dipole as depicted in FIG. 10A using three-gradient x-y tracking system 900 described with reference to FIG. 9.

As illustrated in FIG. 10B, the tracked path of brain dimensions closely follows the actual path as described in FIG. 10A.

In this example, when the magnetic dipole first travels up and to the right from point 1006 to point 1008 via segment 1010, an associated magnetic field will be detected by a three-axis magnetic gradiometer in accordance with aspects of the present invention. As the magnetic dipole travels in the positive x-direction from point 1008 to point 1012 via path 1014, an associated magnetic field will be detected by a three-axis magnetic gradiometer in accordance with aspects of the present invention. As the magnetic dipole travels down and to the right from point 1012 to point 1016 via path 1018, an associated magnetic field will be detected by a three-axis magnetic gradiometer in accordance with aspects of the present invention. Furthermore, as the magnetic dipole travels left and slightly down from point 1016 to point 1020 via path 1022, an associated magnetic field will be detected by a three-axis magnetic gradiometer in accordance with aspects of the present invention. Finally, as the magnetic dipole travels up and to the right from point 1020 to point 1024 via path 1026, an associated magnetic field will be detected by a three-axis magnetic gradiometer in accordance with aspects of the present invention. The tracking is better than one millimeter accuracy and resolution.

An MEG system in accordance with aspects of the present invention may be used, where magnetic field information, external magnetic noise, movement information and synchronization information are received and processed for presenting information for viewing. This will be described in greater detail with reference to FIG. 11A.

Figure 11A:
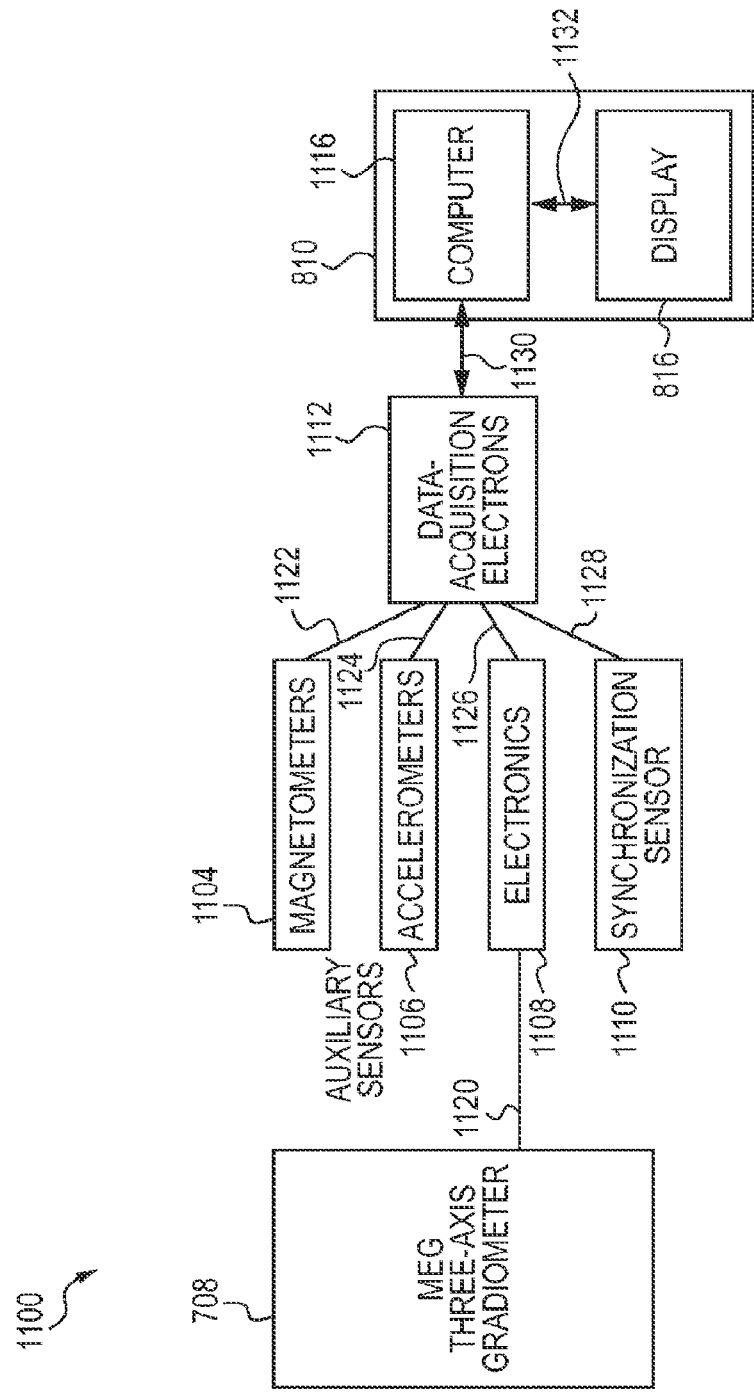
FIG. 11A is an illustration for an example MEG system with one of three three-axis gradiometers, in accordance with an aspect of the present invention.

FIG. 11A is an illustration for an example MEG system 1100 with one of three three-axis gradiometers, in accordance with an aspect of the present invention. To simplify the discussion, only one three-axis gradiometer is shown. However, it would be understood by one of skill in the art that the remaining two of the three-axis gradiometers will be similarly employed.

MEG system 1100 includes three-axis magnetic gradiometer portion 808, a magnetometers portion 1104, an accelerometers portion 1106, an electronics portion 1108, a synchronization sensor portion 1110, a data acquisition portion 1112 and computing device portion 810. Furthermore, computing device portion 810 includes a computer portion 1116 and presentation portion 816.

Electronics portion 1108 receives information from three-axis magnetic gradiometer portion 808 via a communication channel 1120.

Data acquisition portion 1112 receives information from magnetometers portion 1104 via a communication channel 1122, from accelerometers portion 1106 via a communication channel 1124, from electronics portion 1108 via a communication channel 1126 and from synchronization sensor portion 1110 via a communication channel 1128. Computer portion 1116 communicates bi-directionally with data acquisition electronics via a communication channel 1130. Presentation portion 816 communicates bi-directionally with computer portion 1116 via a communication channel 1132.

Three-axis magnetic gradiometer portion 808 detects and communicates information associated with a magnetic field. Magnetometers portion 1104 detects and communicates information associated with external magnetic noise and other anomalies. Accelerometers portion 1106 detects and communicates information associated with movement (e.g., vibration). Electronics portion 1108 provides and interface between three-axis magnetic gradiometers and data acquisition electronics. Synchronization sensor portion 1110 aids in initiation of localization process and may include one or two Electroencephalography (EEG) channels. Data acquisition portion 1112 receives and process information from sensors and other electronics. Computer portion 1116 communicates information for controlling data acquisition electronics and receives, processes information from data acquisition electronics and communicates information for viewing. Presentation portion 816 receives and presents information for viewing and receives communicates information from a user.

In operation, three-axis magnetic gradiometer portion 808 receives magnetic field information and communicates magnetic field information to electronics portion 1108. Magnetometers portion 1104 detects external magnetic noise information and communicates external magnetic information to data acquisition portion 1112. Accelerometers portion 1106 detects movement information and communicates movement information to data acquisition portion 1112. Electronics portion 1108 receives and processes magnetic field information from three-axis magnetic gradiometer and communicates processed information to data acquisition portion 1112. Synchronization sensor portion 1110 receives synchronization information and communicates synchronization information to data acquisition portion 1112.

Data acquisition portion 1112 receives magnetic noise information from magnetometers portion 1104, movement information from accelerometers portion 1106, processed magnetic field information from electronics portion 1108 and synchronization information from synchronization sensor portion 1110. Furthermore, data acquisition portion 1112 processes received information and communicates processed information to computer portion 1116. Computer receives and processes information from data acquisition portion 1112 and presents information for viewing to presentation portion 816. Presentation portion 816 presents information for viewing and receives information from user. Presentation portion 816 communicates information received from user to computer portion 1116. Computer portion 1116 receives and processes information received from presentation portion 816 and communicates information to data acquisition portion 1112.

Since magnetic fields evoked by sensory stimulation of the human brain are orders of magnitude smaller than typical environmental and biological noise at low frequencies, some technique of noise reduction is needed in order to extract biologically induced signals from the measured data. Conventional noise cancellation efforts applied to data similar to those collected in this investigation have usually consisted of signal averaging. While signal averaging provides good results, it requires large amounts of data in order to achieve adequate noise reduction. This can be a serious limitation in investigating biologically evoked responses, in which the concentration of a human subject on a repetitious stimulus is needed. This is even more of a hazard in the case of a medical monitoring tool where the time needed for determining changes in vital life functions may be fatal. Using alternative techniques of noise cancellation in order to reduce the amount of data needed to characterize the evoked response. The objective of filtering associated with this embodiment is to reduce the environmental noise. This noise reduction is achieved by using digital signal processing techniques, primarily an adaptive noise canceller utilizing auxiliary sensors.

There are several sources of noise which contribute to the output of the gradiometer. One is the inherent noise of the gradiometer electronics. Another type of noise source is environmental noise. This is caused by the motion of the system and the magnetometer in the ambient magnetic gradient. These noise sources can be significant for a gradiometer suspended in an urban laboratory.

Building motion, support structure motion and system motion may be measured using linear accelerometers.

Another type of noise is environmental magnetic noise. This is the noise caused by changes in the ambient magnetic gradient. This noise may be caused by motors or by moving metallic objects. The largest environmental magnetic noise source is that of the ambient magnetic field changes at (50-60) Hz due to local power sources. This is normally removed by a notch filter. In general ambient gradient changes are proportional to ambient field changes and can be monitored by a tri-axial fluxgate magnetometer. Fluxgates may also sense environmental motion noise when they are attached to the system since they move with respect to the ambient magnetic vector.

Another type of noise is biologic noise. The gradiometer senses magnetic signals that originate with the subject, but are not related to the evoked signal. Non-limiting methods for monitoring biological noise such as an electric-field sensor (such as a specially located EEG), a secondary gradiometer, or even an accelerometer or a magnetometer attached to the subject. For example, Beta waves are associated with waking activities, Alpha waves are associated with relaxed wakefulness, Occipital waves are associated with the occipital portion of the brain, Theta waves is associated with creativity, Delta waves associated with deep sleep, and Epileptic waves are associated with a person diagnosed with epilepsy. This will be described with reference to FIG. 11B.

Figure 11B:
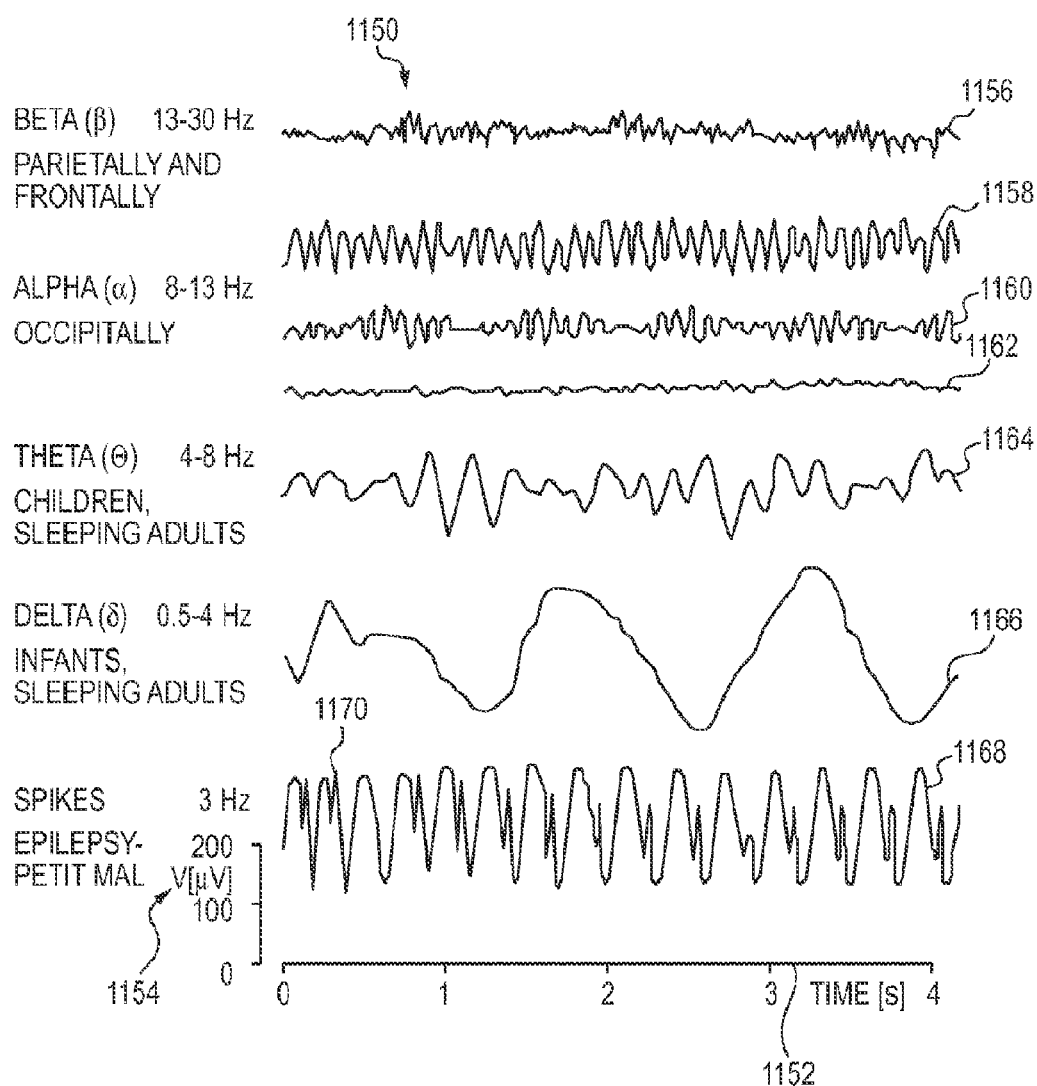
FIG. 11B is an illustration for an example template graph for a three-axis magnetic gradiometer, in accordance with an aspect of the present invention.

FIG. 11B is an illustration for an example template graph 1150 for a three-axis magnetic gradiometer, in accordance with an aspect of the present invention.

Template graph 1150 includes an x-axis 1152 representing time with units of seconds and a y-axis 1154 representing voltage with units of micro volts.

A beta signal 1156 represents Beta brain waves. An alpha signal 1158 represents Alpha brain waves. An occipital signal 1160 represents Occipital brain waves. A theta signal 1162 represents Theta brain waves for children sleeping. A theta signal 1164 represents Theta brain waves for adults sleeping. A delta signal 1166 represents Delta brain waves for infants and sleeping adults. An epileptic signal 1168 represents Epileptic signals associated with a person with Epilepsy Beta signal 1156, alpha signal 1158, occipital signal 1160, theta signal 1162, theta signal 1164, delta signal 1166 are brain waves associated with a normal healthy person. Epileptic signal 1168 is a brain wave associated with a person diagnosed with epilepsy with the associated signal exhibiting a multiplicity of spikes with a sampling noted as a spike 1170.

As an example, computing device portion 810 receives and processes signals in order to determine normal or abnormal brain wave activity. Furthermore, in order to perform the classification of normal versus abnormal, computing device portion 810 is trained in order to detect normal versus abnormal. Furthermore, as an example, training may include determining feature vectors for normal/abnormal signals and developing classifiers for determining the difference between normal and abnormal.

As an example, feature vectors would be created for Beta signal 1156, Alpha signal 1158, Occipital signal 1160, Theta signal 1162, Theta signal 1164, Delta signal 1166 and Epileptic signal 1168. The classifier would classify Beta signal 1156, Alpha signal 1158, Occipital signal 1160, Theta signal 1162, Theta signal 1164 and Delta signal 1166 as normal and would classify Epileptic signal 1168 as abnormal.

FIG. 11B is an illustration for an example template graph illustrating normal and abnormal brain wave activity which may be used for classifying normal versus abnormal brain wave activity.

Figure 12:
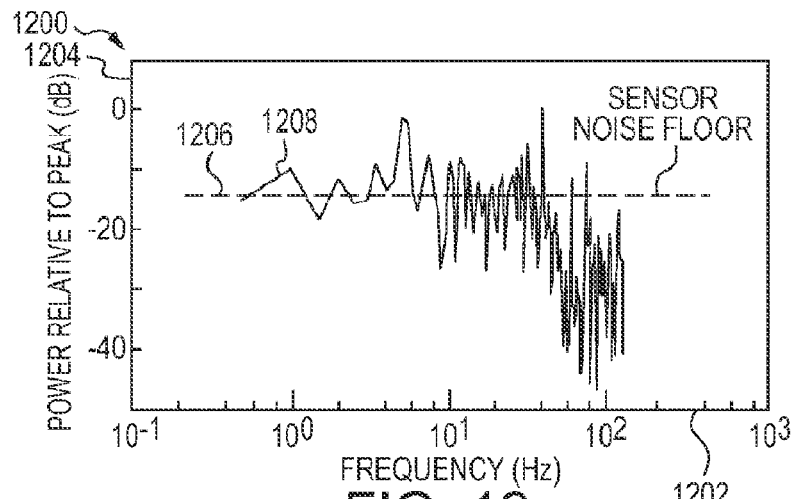
FIG. 12 is an illustration for an example noise power spectrum graph for a single SDG-, in accordance with an aspect of the present invention.

FIG. 12 is an illustration for an example noise power spectrum graph 1200 for a three-axis magnetic gradiometer, in accordance with an aspect of the present invention. To simplify the discussion, only one three-axis gradiometer is shown in the following discussion of FIGS. 12-27. However, it would be understood by one of skill in the art that the remaining two of the three-axis gradiometers will be similarly employed.

Noise power spectrum graph 1200 includes an x-axis 1202 representing frequency with units of Hertz and a y-axis 1204 representing noise power relative to peak noise with units of decibels.

A sensor noise floor 1206 is located around a y-axis value of −15 dB and exists from an approximate x-value of 0.3 Hz to an approximate x-value of 500 Hz.

A line 1208 initiates at an x-axis value of approximately 0.5 Hertz with a y-axis value of approximately −15 dB (i.e. sensor noise floor 1206). As the x-axis frequency increases from 0.3 Hertz to 50 Hz, the y-axis value is typically around −15 dB (i.e. sensor noise floor 1206). For x-axis frequencies greater than 50 Hz, the y-axis value drops below −15 dB (i.e. sensor noise floor 1206) and is typically in the range of −30 dB.

This illustrates the noise power spectrum for the gradiometer for a section of data in which noise sources are small. The gradiometer output appears to be approximately at the sensor noise level.

Two types of data are presented. The first type of data consists of gradiometer and auxiliary sensor data with no evoked response or biologic noise data. With these data the noise present is characterized and a parametric study of the adaptive noise canceller is performed. The second type of data is like the first, but with a small-amplitude 10 Hz sine wave imposed on the gradiometer output. (A 10 Hz sine wave signal is applied on a loop located near the gradiometer sensor loops.) The signal has approximately the same size as the noise present. These data provided a test case to determine how well the adaptive noise canceller could perform on data, when the signal-to-noise ratio is <1.

Multiple sensors capable of distinguishing sources of magnetic noise and the short duration of the biologically induced signal indicate that adaptive digital filtering may be used for noise cancellation.

With a priori knowledge of the characteristics of the unwanted noise (e.g. 60 Hz noise from power lies is common in magnetic data), then a fixed weight filter may be implemented which selectively removes power at the frequencies at which noise is present and passes those frequencies containing the signal.

An adaptive filter requires no a priori knowledge of the noise, but instead learns the noise characteristics from reference sensor inputs. The frequency response of the adaptive filter changes as it acquires knowledge of the noise.

The frequencies at which the reference sensors indicate noise is present are inhibited proportionally to the relative power at those frequencies. The determination of the filter weights depends upon the correlation between the measured data in the primary and reference channels. The signal is expected to be present in the primary and not in the reference; hence the signal theoretically passes through the filter unmodified.

The power of an adaptive filter is associated with the filter weights, and hence the frequency response of the filter, are allowed to change or adapt, in time. Thus, if the noise is non-stationary, that is, if the statistics of the noise vary during the measurement, the filter varies in an attempt to follow the statistics and provide maximum reduction of the noise. This advantage, however, has an associated drawback. When the character of the noise changes, the filter requires a nonzero amount of time to react. Since the modification to the filter is not instantaneous, the adaptation process itself adds noise, termed misadjustment noise. While misadjustment noise is not eliminated, it can be minimized by the use of an appropriately chosen filter.

The simple adaptive filter used here utilizes a Least Mean Square (LMS) algorithm. Of course, many other adaptive filters types, as well as spectral techniques, may be used. Two parameters are chosen: the length of the filter and the feedback constant. The filter length determines the number of samples needed to specify the filter response and is also equal to the number of filter weights. The feedback constant determines the gain in the feedback loop which governs how quickly the filter weights are allowed to adapt. The choice of appropriate values for the two free parameters is based primarily on experience with the particular data of interest and is developed here via parametric studies. Increasing the number of filter weights generally improves the noise canceller performance, but can also increase misadjustment noise. Misadjustment noise also appears to increase with larger values of the feedback constant. The analysis indicated that, within certain limits, the noise cancellation results are not particularly sensitive to the length of the filter, but varied considerably with the choice of the feedback constant.

The results shown here were generated by using adaptive filters with feedback constants varying from 0.1 to 0.5 and lengths corresponding to 20 to 35 weights.

Along with the 35 Hz low-pass analog filter applied to the data prior to digitization, the data containing the added 10 Hz signal is digitally low-pass filtered prior to being adaptively filtered. The 3 dB point of the filter is configured for 15 Hz. Implementation of the digital low-pass filter in addition to the analog low-pass filter served to further reduce power levels for frequencies above 15 Hz. Without this additional filtering, misadjustment noise, due to the subsequent implementation of the adaptive filter, sufficiently raised power levels so as to obscure the 10 Hz signal. Similar filtering may be used for data containing evoked responses. The other results presented here are noise measurements and are not low-pass filtered prior to implementation of the adaptive filter.

Techniques for reduction of noise associated with movement (e.g. vibration) are discussed in further detail with reference to FIGS. 13-16.

Figure 13:
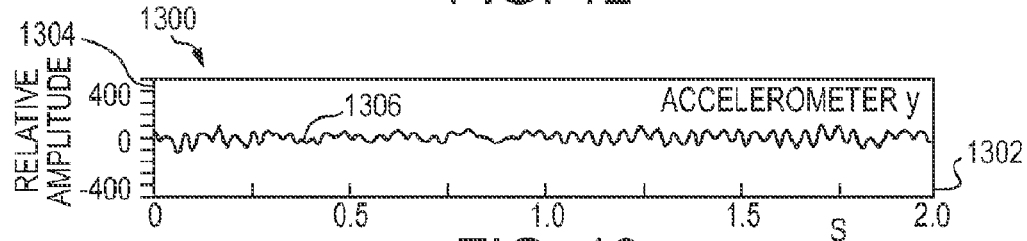
FIG. 13 is an illustration for an example accelerometer graph, in accordance with an aspect of the present invention.

FIG. 13 is an illustration for an example accelerometer graph 1300, in accordance with an aspect of the present invention.

Accelerometer graph 1300 includes an x-axis 1302 representing time in units of seconds and a y-axis 1304 representing relative amplitude with unites of volts. The length of x-axis 1302 is two seconds.

The amplitude of a line 1306 exhibits an oscillatory pattern. Line 1306 represents movement associated with noise. Line 1306 exhibits periods of increased noise from 0 seconds to approximately 0.25 seconds and from approximately 1 second to 2 seconds.

FIG. 13 is an illustration for an example accelerometer graph where noise is reduced for a certain time period.

Figure 14:
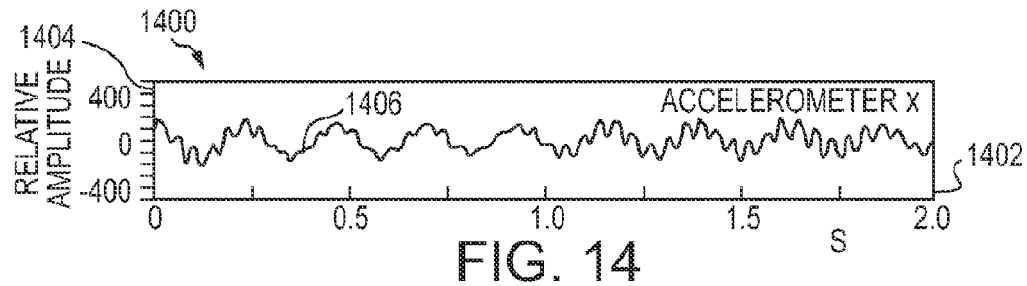
FIG. 14 is an illustration for an example accelerometer graph, in accordance with an aspect of the present invention.

FIG. 14 is an illustration for an example accelerometer graph 1400, in accordance with an aspect of the present invention.

Accelerometer graph 1400 includes an x-axis 1402 representing time in units of seconds and a y-axis 1404 representing relative amplitude with unites of volts. The length of x-axis 1402 is two seconds.

A line 1406 exhibits two oscillatory noise signals superimposed. The first noise signal is similar to the signal as described with reference to FIG. 13. The second noise signal has larger amplitude and has a period of approximately 1 second.

FIG. 14 is an illustration for an example accelerometer graph with two oscillatory signal superimposed.

Figure 15:
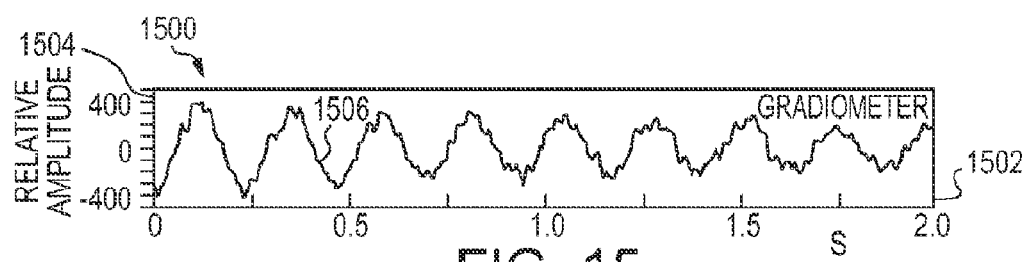
FIG. 15 is an illustration for an example three-axis magnetic gradiometer graph, in accordance with an aspect of the present invention.

FIG. 15 is an illustration for an example three-axis magnetic gradiometer graph 1500, in accordance with an aspect of the present invention.

Three-axis magnetic gradiometer graph 1500 includes an x-axis 1502 representing time in units of seconds and a y-axis 1504 representing relative amplitude with unites of volts. The length of x-axis 1502 is two seconds.

A line 1506 includes a plurality of superimposed signals. Line 1506 includes small amplitude noise and large amplitude noise with the small amplitude noise similar to the noise as described with reference to FIG. 13 and the large amplitude noise as described with reference to FIG. 14.

FIG. 15 is an illustration for an example three-axis magnetic gradiometer graph where noise is received by a three-axis magnetic gradiometer.

Figure 16:
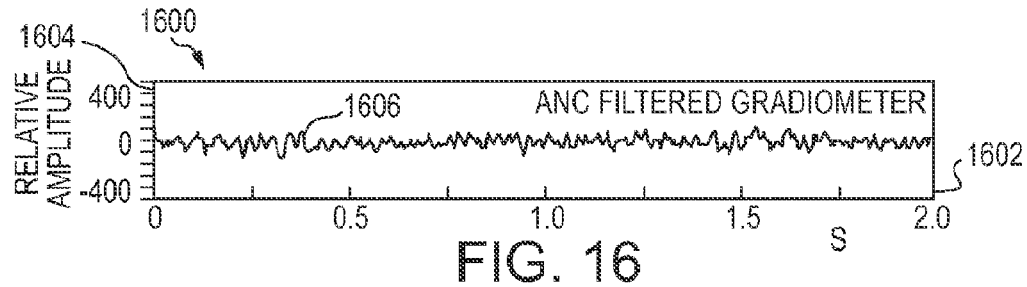
FIG. 16 is an illustration for an example adaptively filtered single MEG channel-graph, in accordance with an aspect of the present invention.

FIG. 16 is an illustration for an example adaptively filtered three-axis magnetic gradiometer graph 1600, in accordance with an aspect of the present invention.

Adaptively filtered three-axis magnetic gradiometer graph 1600 includes an x-axis 1602 representing time in units of seconds and a y-axis 1604 representing relative amplitude with unites of volts. The length of x-axis 1602 is two seconds.

A line 1606 is presented which has reduced noise as described with reference to FIG. 13 and the noise described with reference to FIG. 15. The noise has been reduced via an adaptive filter.

FIG. 16 is an illustration for an example adaptively filtered three-axis magnetic gradiometer graph where accelerometer noise has been reduced.

Simultaneous measurements from the accelerometers as presented by FIGS. 13-14 enabled the identification and reduction of motion noise from the gradiometer. The correlation between the x-accelerometer as presented by FIG. 14 and the gradiometer as presented by FIG. 15 suggests a large amount of motion noise at a nominal frequency of 4 HZ in the gradiometer data. FIG. 16 illustrates the result of adaptively filtering the gradiometer data using the x and y accelerometers (FIGS. 13-14) as reference sensors. The presence, and subsequent removal, of motion-induced magnetic noise in the gradiometer is evident both in the time series as presented in FIG. 16 and also in the power spectra of the filtered and unfiltered gradiometer data described with reference to FIG. 17 below.

Figure 17:
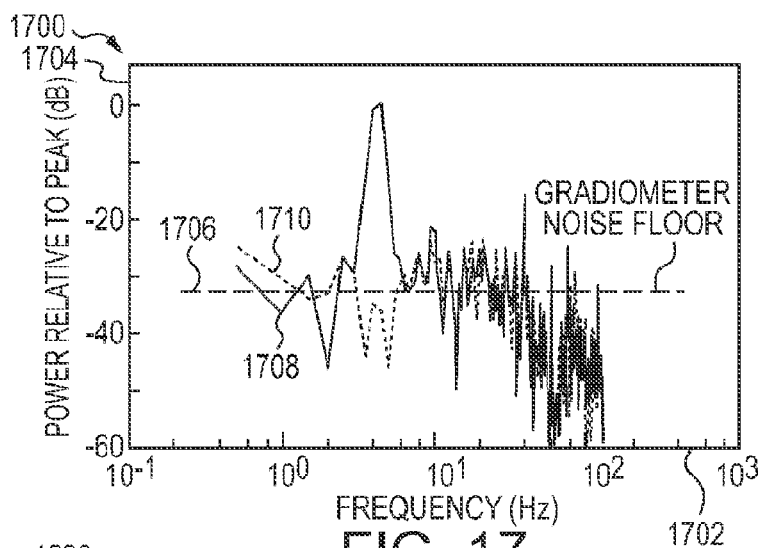
FIG. 17 is an illustration for an example noise power spectrum graph for a single MEG channel-, in accordance with an aspect of the present invention.

FIG. 17 is an illustration for an example noise power spectrum graph 1700 for a three-axis magnetic gradiometer, in accordance with an aspect of the present invention.

A line 1708 represents magnetometer data and a dotted line 1710 represents an adaptive noise cancelled signal.

The noise power from the unfiltered signal as illustrated by line 1708 has been reduced by approximately 35 dB as presented by dotted line 1710 representing the adaptively filtered signal. Misadjustment noise, which shows up as increased power levels in the power spectra of the filtered data, is relatively minimal in this case, indicating that appropriate values of the feedback constant and filter length are chosen.

FIG. 17 is an illustration for an example noise power spectrum graph where motion noise has been reduced via adaptive filtering using an accelerometer as the reference signal. Noise and causality can also be determined with the use of other spectral techniques such as multiple, cross spectral coherence.

Combined environmental motion noise and environmental magnetic noise will be described in further detail with reference to FIGS. 18-22.

Figure 18:
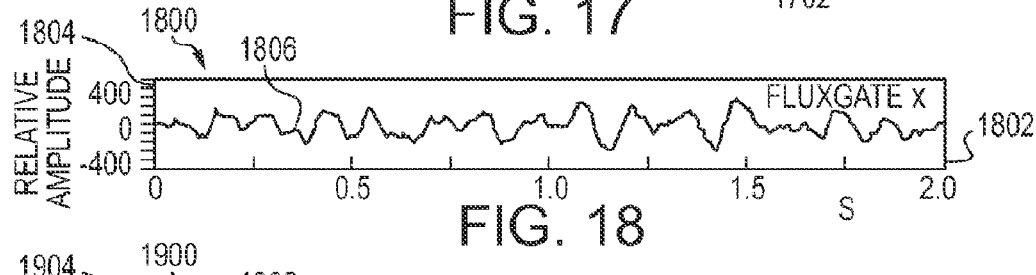
FIG. 18 is an illustration for an example fluxgate graph, in accordance with an aspect of the present invention.

FIG. 18 is an illustration for an example fluxgate graph 1800, in accordance with an aspect of the present invention.

Fluxgate graph 1800 includes an x-axis 1802 representing time in units of seconds and a y-axis 1804 representing relative amplitude with unites of volts. The length of x-axis 1802 is two seconds. FIG. 18 demonstrates that the two second sampling interval may be resolved into several picoseconds with new fast sampling oscilloscopes, thus allowing better spatial track resolution.

Figure 19:
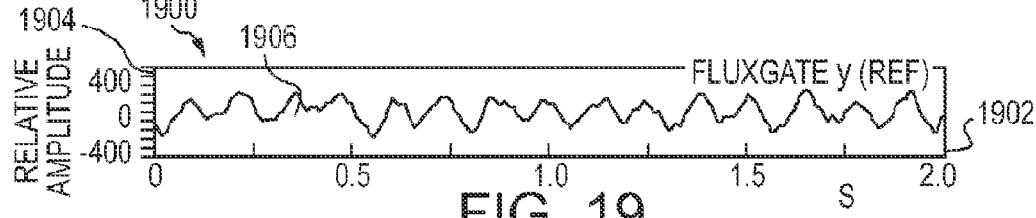
FIG. 19 is an illustration for an example fluxgate graph, in accordance with an aspect of the present invention.

FIG. 19 is an illustration for an example fluxgate graph 1900, in accordance with an aspect of the present invention.

Fluxgate graph 1900 includes an x-axis 1902 representing time in units of seconds and a y-axis 1904 representing relative amplitude with unites of volts. The length of x-axis 1902 is two seconds.

Figure 20:
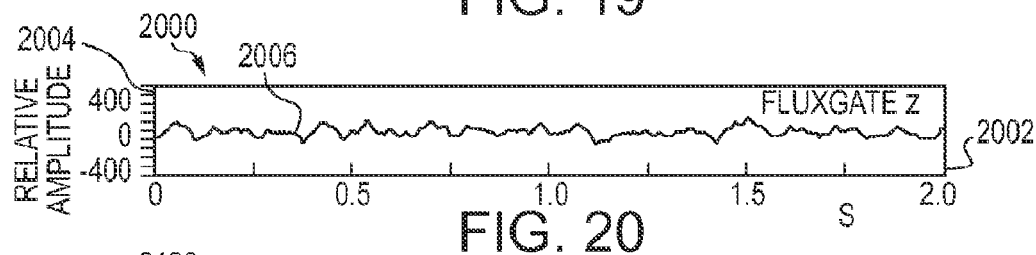
FIG. 20 is an illustration for an example fluxgate graph, in accordance with an aspect of the present invention.

FIG. 20 is an illustration for an example fluxgate graph 2000, in accordance with an aspect of the present invention.

Fluxgate graph 2000 includes an x-axis 2002 representing time in units of seconds and a y-axis 2004 representing relative amplitude with unites of volts. The length of x-axis 2002 is two seconds.

Figure 21:
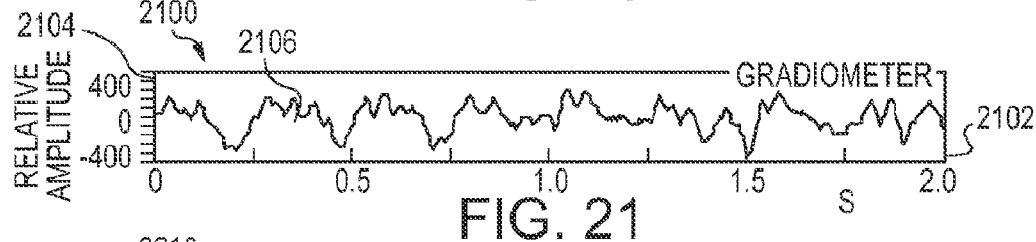
FIG. 21 is an illustration for an example single MEG channel graph, in accordance with an aspect of the present invention.

FIG. 21 is an illustration for an example single-axis magnetic gradiometer graph 2100, in accordance with an aspect of the present invention.

Single-axis magnetic gradiometer graph 2100 includes an x-axis 2102 representing time in units of seconds and a y-axis 2104 representing relative amplitude with unites of volts. The length of x-axis 2102 is two seconds.

Figure 22:
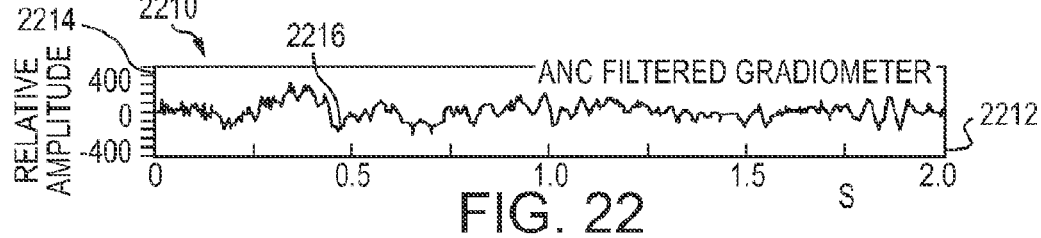
FIG. 22 is an illustration for an example adaptively filtered single MEG channel graph, in accordance with an aspect of the present invention.

FIG. 22 is an illustration for an example adaptively filtered singles magnetic gradiometer graph 2200, in accordance with an aspect of the present invention.

Adaptively filtered single-axis magnetic gradiometer graph 2200 includes an x-axis 2202 representing time in units of seconds and a y-axis 2204 representing relative amplitude with unites of volts. The length of x-axis 2202 is two seconds.

Figure 23:
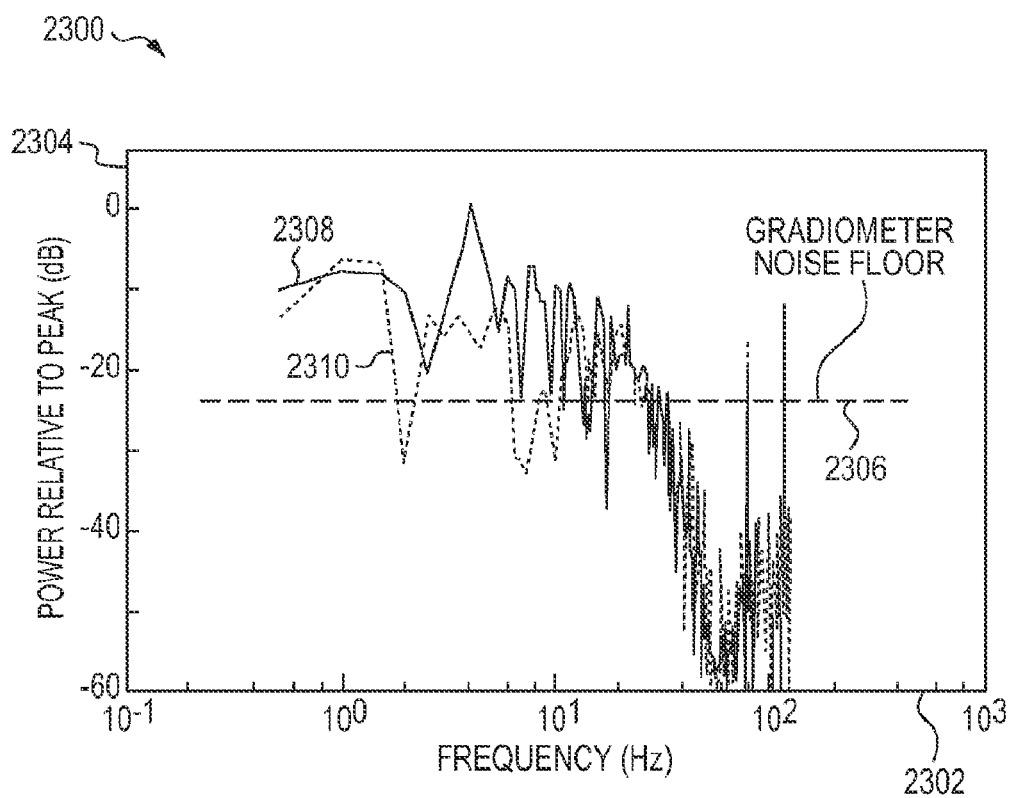
FIG. 23 is an illustration for an example noise power spectrum graph for a single MEG channel-in accordance with an aspect of the present invention.

FIG. 23 is an illustration for an example noise power spectrum graph 2300 for a single-axis magnetic gradiometer, in accordance with an aspect of the present invention.

A line 2308 represents magnetometer data and a dotted line 2310 represents an adaptive noise cancelled signal.

In this case, the y-fluxgate magnetometer as illustrated in FIG. 19 was chosen as the reference to the adaptive filter.

In this case, as may be observed from the power spectra of the filtered data as presented by dotted line 2310 and the unfiltered data as presented by line 2308, that approximately 15 dB of noise has been removed in the 4 Hz region and also approximately 10 dB of noise has been reduced in a band near 10 Hz. The 4 Hz noise is motion-induced magnetic noise (the fluxgate magnetometer is somewhat sensitive to motion). However, the noise removed near 10 Hz is, probably not motion-induced magnetic noise, since filtering with any or all of the accelerometers does not significantly reduce power in the 10 Hz region. The performance for this case in terms of misadjustment is not as good as observed with respect to FIGS. 13-17 using accelerometers. By comparing the time domain filtered signal as illustrated in FIG. 22 and the time domain unfiltered signal as presented in FIG. 21 an increase in the higher-frequency components in the filtered data may be observed. Although different parameters have been chosen to specify the filter, the primary difference between this and the previous case described with reference to FIGS. 13-17 are the statistical characteristics of the noise being removed. The magnetic noise measure by the fluxgate and removed from the gradiometer included higher-frequency components than did the motion noise removed by the accelerometer. Most likely, the filter weights are attempting to change more drastically form one time step to the next and hence the misadjustment noise is more pronounced.

FIG. 23 is an illustration for an example noise power spectrum graph illustrating noise reduction using an adaptive filter with a fluxgate as the reference signal.

Reduction of noise with an injected 10 Hz sine wave noise signal will be described in further detail with reference to FIGS. 24-26. Injected 10 Hz sine wave is injected via a loop of wire located near the gradiometer.

Figure 24:
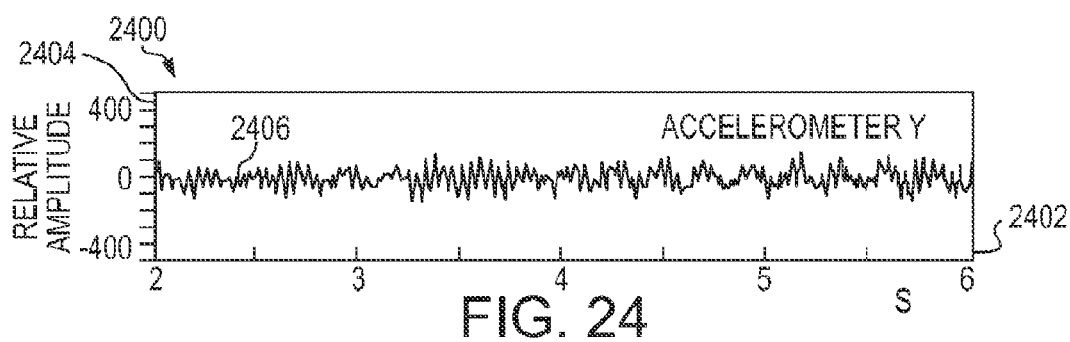
FIG. 24 is an illustration for an example accelerometer graph, in accordance with an aspect of the present invention.

FIG. 24 is an illustration for an example accelerometer graph 2400, in accordance with an aspect of the present invention.

Accelerometer graph 2400 includes an x-axis 2402 representing time in units of seconds and a y-axis 2404 representing relative amplitude with unites of volts. The length of x-axis 2402 is two seconds.

Figure 25:
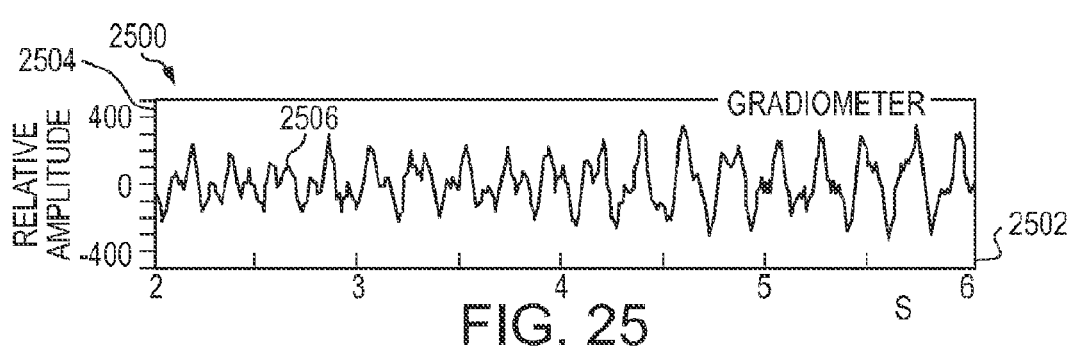
FIG. 25 is an illustration for an example single MEG channel graph, in accordance with an aspect of the present invention.

FIG. 25 is an illustration for an example single-axis magnetic gradiometer graph 2500, in accordance with an aspect of the present invention.

Single-axis magnetic gradiometer graph 2500 includes an x-axis 2502 representing time in units of seconds and a y-axis 2504 representing relative amplitude with unites of volts. The length of x-axis 2502 is two seconds.

Figure 26:
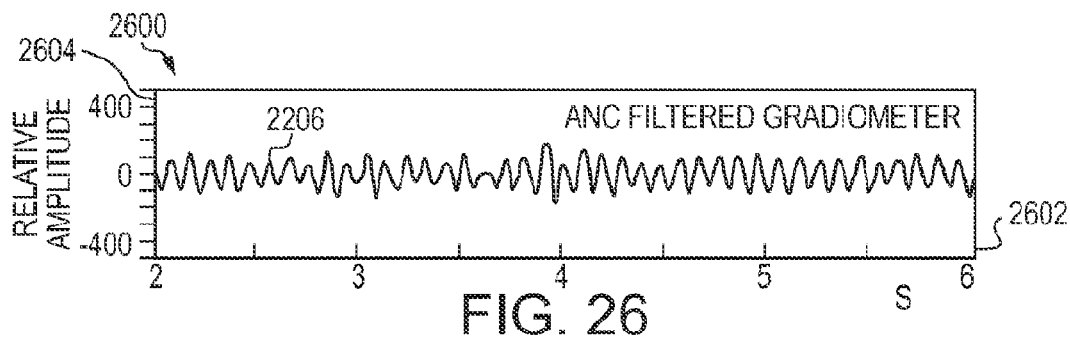
FIG. 26 is an illustration for an example adaptively filtered single MEG channel graph, in accordance with an aspect of the present invention.

FIG. 26 is an illustration for an example adaptively filtered single-axis magnetic gradiometer graph 2600, in accordance with an aspect of the present invention.

Adaptively filtered single-axis magnetic gradiometer graph 2600 includes an x-axis 2602 representing time in units of seconds and a y-axis 2604 representing relative amplitude with unites of volts. The length of x-axis 2602 is two seconds.

Figure 27:
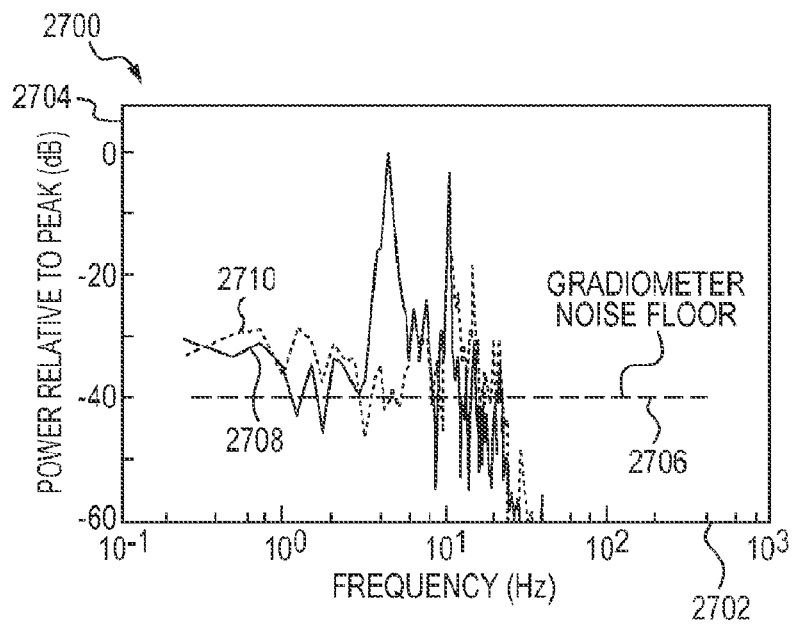
FIG. 27 is an illustration for an example noise power spectrum graph for a single MEG channel, in accordance with an aspect of the present invention.

FIG. 27 is an illustration for an example noise power spectrum graph 2700 for a single-axis magnetic gradiometer, in accordance with an aspect of the present invention.

A line 2708 represents magnetometer data and a dotted line 2710 represents an adaptive noise cancelled signal.

FIGS. 24-26 present four seconds of time series data for the y-accelerometer and the gradiometer with a 10 Hz signal added. From observing the time series data in FIGS. 24-26, it is not clear that cancellation using the y-accelerometer provides enhancement of the signal relative to the noise. Improved results were obtained by first digitally low-pass filtering the data (3 dB point at 15 Hz). By using the resultant filtered gradiometer data as the primary and the y-accelerometer as the reference, the adaptive filter was then implemented. The filtered gradiometer time series as presented by FIGS. 24-26 illustrate the removal of the noise from the 10 Hz signal as presented by FIG. 25 leaving the 10 Hz signal with reduced noise as illustrated by the adaptive filtered signal of FIG. 26. Furthermore, the signal was pulled out of the noise and with a reduction in noise power of approximately 40 dB. Furthermore, very little misadjustment noise is added partially a result of the pre-filtering by the 15 Hz low-pass filter. The primary effect of the 15 Hz low-pass filter is to smooth the data and, therefore, reduce the jitter in the filter weights that result in misadjustment noise.

FIG. 27 is an illustration for an example noise power spectrum graph where noise is reduced for enhancing an injected signal.

Figure 28:
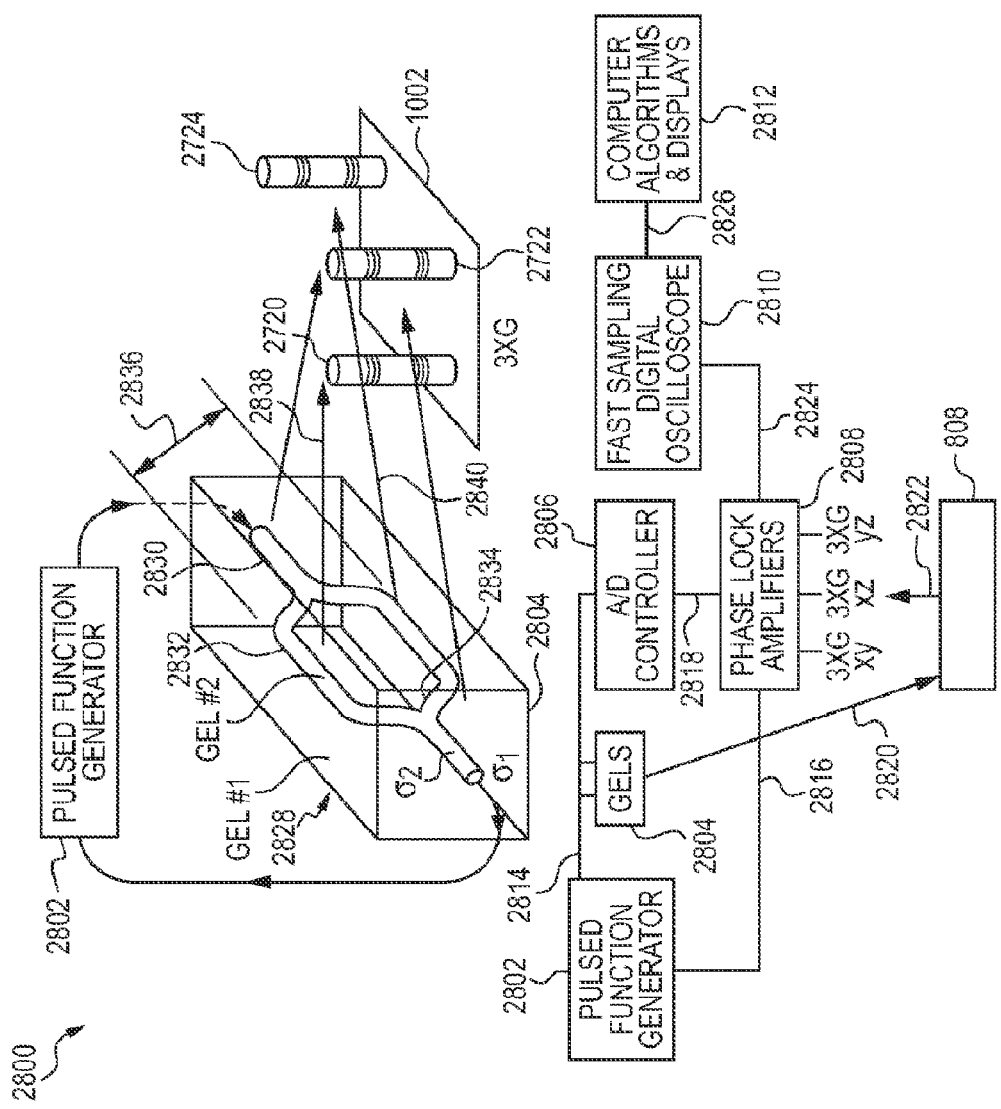
FIG. 28 is an illustration for an example In-Vitro development system, in accordance with an aspect of the present invention.

FIG. 28 is an illustration for an example development system 2800, in accordance with an aspect of the present invention.

IN-VITRO Development system 2800 includes three-axis magnetic gradiometer portion 808, a function generator 2802, a gel portion 2804, an A/D controller 2806, a phase lock amplifiers portion 2808, a digital oscilloscope 2810 and a computing device 2812.

Gel portion 2804 and A/D controller 2806 receive a signal from function generator 2802 via a communication channel 2814. Phase lock amplifiers portion 2808 receives a signal from function generator 2802 via a communication channel 2816 and receives a signal from A/D controller 2806 via a communication channel 2818. Three-axis magnetic gradiometer portion 808 receives a magnetic field 2820 from gel portion 2804. Phase lock amplifiers portion 2808 receives signals from three-axis magnetic gradiometer portion 808 via a communication channel 2822.

Digital oscilloscope 2810 receives a signal from phase lock amplifiers portion 2808 via a communication channel 2824. Computing device 2812 receives information from digital oscilloscope 2810 via a communication channel 2826. Development system 2800 enables validating, testing and development of systems associated with three-axis magnetic gradiometer portion 808. Function generator 2802 generates an electrical signal. In an example embodiment, function generator 2802 provides a pulsed signal. Gel portion 2804 provides paths for electrical currents and may calibrated. A/D controller 2806 provides conversion of continuous electrical signals to a discrete or sampled representation of the continuous signal.

Phase lock amplifiers portion 2808 provides output signals with phases related to the phases of the received signals, respectively. Digital oscilloscope 2810 presents a digital representation for a received analog signal. Computing device 2812 receives and process information for presenting information for viewing.

Development system 2800 enables validation of the physics associated with three-axis magnetic gradiometer portion 808. Furthermore, development system 2800 enables examination of spurious current paths. Furthermore, development system 2800 provides capability for optimizing algorithms associated with three-axis magnetic gradiometer portion 808. Furthermore, development system 2800 enables testing of three-axis magnetic gradiometer portion 808 with respect to time, tracking and registration. Development system enables testing and development for discrimination between a plurality of trajectories of electrical current.

Gel portion 2804 includes a low conductance gel 2828 and a high conductance gel 2830. In this example, low conductance gel 2828 has a lower conductance than high conductance gel 2830. High conductance gel 2830 is contained within low conductance gel 2828. High conductance gel 2830 includes a path 2832 and a path 2834. Path 2832 and path 2834 traverse in parallel and are separated by a distance 2836.

In operation, a signal initiates at function generator 2802 and travels into gel portion 2804 and into A/D controller 2806. After signal enters gel portion 2804, the signal traverses the path associated with high conductance gel 2830, since the conductivity of high conductance gel 2830 is greater than the conductivity of low conductance gel 2828. Furthermore, a portion of the signal traverses path 2832 and a portion of the signal traverses path 2834. The traversing of the signal through path 2832 generates a magnetic field 2838 and the traversing of the signal through path 2834 generates a magnetic field 2840. Magnetic field 2838 and magnetic field 2840 are received by three-axis magnetic gradiometer portion 808. The three-dimensional information received by three-axis magnetic gradiometer portion 808 and the digitized signal received from the A/D controller are presented to phase lock amplifiers portion 2808. Phase lock amplifiers portion 2808 synchronizes with the received signals and presents the synchronized signals to digital oscilloscope 2810. Digital oscilloscope 2810 receives synchronized signals and provides oscilloscope functions. Computing device 2812 receives, processes presents information from digital oscilloscope 2810 for tracking the movement of the signal as it traverses gel portion 2804.

FIG. 28 is an illustration for an example development system by which signals may be applied to a gel for which the magnetic fields associated with the signal may be received, processed and presented for viewing.

Figure 29:
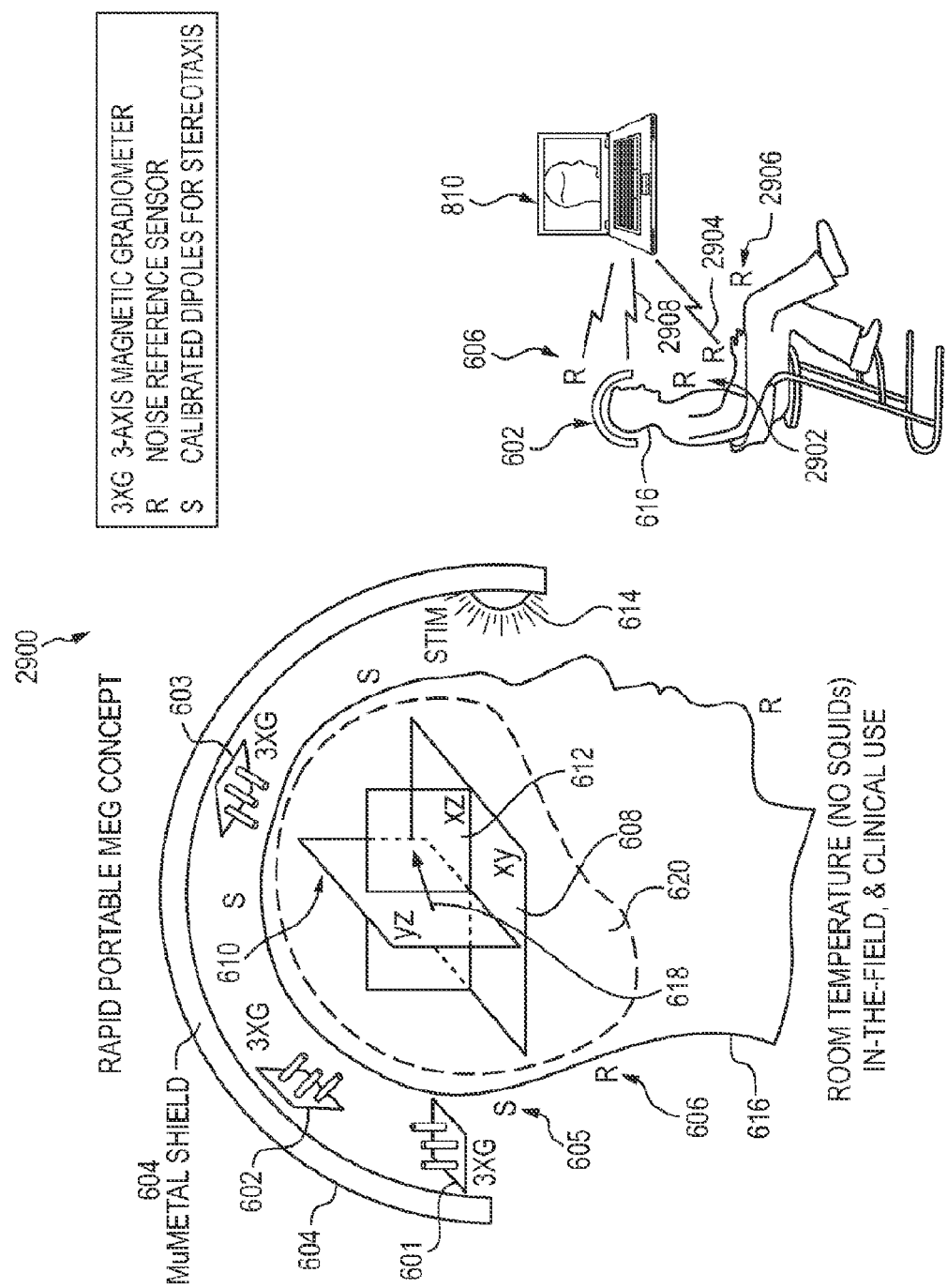
FIG. 29 is an illustration for an example MEG system, in accordance with an aspect of the present invention.

FIG. 29 is an illustration for an example MEG system 2900, in accordance with an aspect of the present invention.

MEG system 2900 includes MEG sensor portion 600, computing device portion 810, a motion sensor 2902, a motion sensor 2904 and a motion sensor 2906.

Computing device portion 810 communicates bi-directionally with MEG sensor portion 600 via a communication channel 2908.

MEG system 2900 generates stimulus for application to head 616 or a body associated with head 616 and receives, processes and presents information for viewing associated with applied stimulus.

Motion sensor 2902 performs motion detection associated with the person's body functions and communicates the detected motion information to computing device portion 810 via communication channel 2908. Non-limiting examples of body functions include heart beat and breathing.

Motion sensor 2904 performs motion detection associated with the person's hand and communicates the detected motion information to computing device portion 810 via communication channel 2908.

Motion sensor 2906 performs motion detection associated with the person's leg and communicates the detected motion information to computing device portion 810 via communication channel 2908.

Motion sensors 2902, 2904 and 2906 enable detection and removal of false signals. For example, a person being analyzed may inadvertently move a hand during the analysis. The system detects the inadvertent move and removes information associated with the inadvertent move from the analysis.

In operation, computing device portion 810 informs, via communication channel 2908, MEG sensor portion 600 to generate stimulus via stimulus 614. Furthermore, stimulus 614 generates and applies stimulus 614 to head 616 for body associated with head 616. Head 616 receives stimulus 614 and stimulus 614 is converted to electrical representation 618 of stimulus. Electrical representation 618 of stimulus 614 traverses head 616. First three-axis magnetic gradiometer portion 601, second three-axis magnetic gradiometer portion 602 and third three-axis magnetic gradiometer portion 603 detects magnetic fields and noise associated with the movement of electrical representation 618. Furthermore, noise reference sensor 606 detects information associated with noise. Furthermore, motion sensors 2902, 2904 and 2906 detect motion associated with body functions, hand and leg, respectively and communicate the motion information to computing device portion 810. Furthermore, MEG sensor portion 600 communicates information received from first three-axis magnetic gradiometer portion 601, second three-axis magnetic gradiometer portion 602, third three-axis magnetic gradiometer portion 603 and noise reference sensor 606 to computing device portion 810. Computing device portion 810 receives information from MEG sensor portion 600 and motion sensors 2902, 2904 and 2906 and then processes the information. As a non-limiting example of processing, unwanted or inadvertent movement information associated with motion sensors 2902, 2904 and 2906 are removed from information for performing the analysis. Furthermore, the results of the analysis are presented for viewing. For example, an athlete may suffer head related injury symptoms during a football game, wherein MEG system 2900 may be used for diagnosis and treatment.

In other embodiments, MEG sensor portion 600 may be used to perform fetal monitoring. For fetal monitoring, MEG sensor portion 600 is configured for receiving information from internal to a woman's womb.

FIG. 29 is an illustration for an example MEG system where a stimulus is applied to a person and the magnetic fields associated the person's electrical representations of the applied stimulus are processed.

Figure 30:
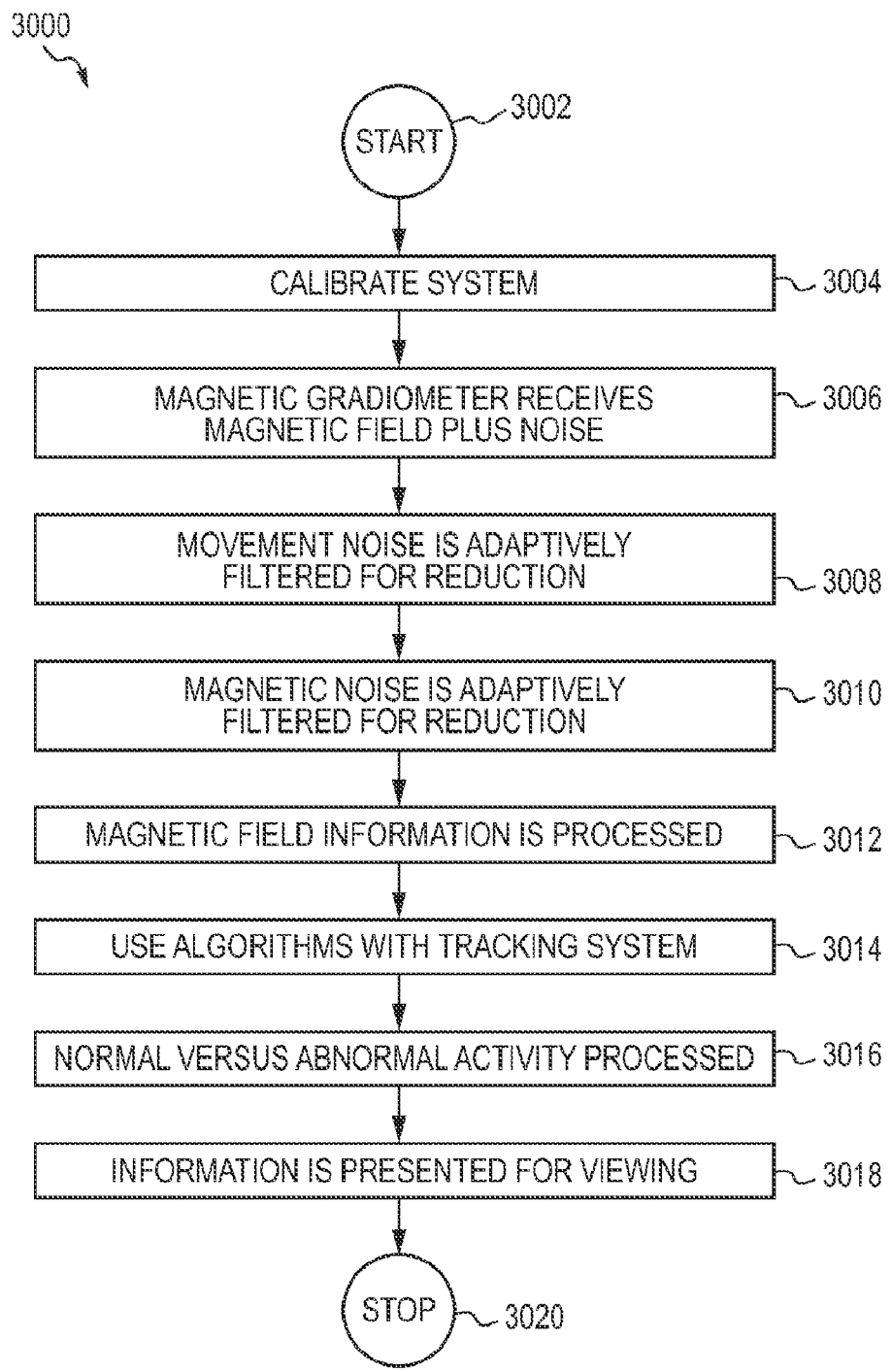
FIG. 30 illustrates an example method for operation of an example MEG system, in accordance with an aspect of the present invention.

FIG. 30 illustrates an example method 3000 for operation of an example MEG system, in accordance with an aspect of the present invention.

Method 3000 starts (S3002) with performance of system calibration (S3004).

Calibration is performed to ensure system is operating correctly. For calibration, known magnetic fields are provided and measured by the system for configuring system for operation. For example, as described with reference to FIG. 29, magnetic dipoles (e.g. magnetic dipole 605 as described with reference to FIG. 6) are activated with gradiometers (e.g. first three-axis magnetic gradiometer portion 601 as described with reference to FIG. 6) detecting magnetic field of the magnetic dipoles and communicating the magnetic field information to computing device portion 810 described with reference to FIG. 8 for performing calibration.

Returning to FIG. 30, then three-axis magnetic gradiometer receives magnetic field plus noise (S3006).

As described with reference to FIG. 29, three-axis magnetic gradiometers (e.g. first three-axis magnetic gradiometer portion 601 (FIG. 6)) receive magnetic fields as a result of electrical currents located within in head 616 (FIG. 6) and noise as a result of the external environment. Furthermore, the received magnetic information is communicated to computing device portion 810 (FIG. 8). For example, the three-axis magnetic gradiometers may detect a magnetic field due to a person detecting a light being turned on, as well as detect magnetic noise associated with electrical power and/or movement noise associated with an air conditioner.

Returning to FIG. 30, then movement noise is adaptively filtered for reduction (S3008).

Sensors detect movement noise (e.g. noise reference sensor 606 as described with reference to FIG. 6). Furthermore, the movement noise (e.g. motion sensor 2902 (FIG. 29)) is communicated to computing device portion 810 (FIG. 8) in order for movement noise to be reduced using example techniques described with reference to FIGS. 12-16. For example, vibration noise associated with an air conditioner may be received by the system and reduced. As another example, noise associated with a person inadvertently moving a hand may be received and removed.

Returning to FIG. 30, then magnetic noise is adaptively filtered for reduction (S3010).

Sensors detect magnetic noise (e.g. noise reference sensor 606 as described with reference to FIG. 6). Furthermore, the magnetic noise is communicated to computing device portion 810 (FIG. 8) in order for magnetic noise to be reduced using example techniques described with reference to FIGS. 17-22. For example, magnetic noise associated with the electrical power may be received by the system and reduced.

Returning to FIG. 30, then magnetic field information is processed (S3012).

Magnetic field information with reduced noise is processed by computing device portion 810 (FIG. 8) in order to determine the movement of electrical current through head 616 (FIG. 6). For example, a person may hear a noise with the resulting electrical currents in the brain producing magnetic fields which are detected and processed for determining the trajectory of the electrical current.

Returning to FIG. 30, then processors using tracking algorithms (S3014).

Any known tracking algorithm may be used that is intended to accurately detect, discriminate and track the movement of magnetic dipoles. Once obtained, theses algorithms may be implemented in a processor for carrying out the algorithm. Non-limiting example algorithms include adaptive filtering techniques to remove motion and magnetic noises. For example, an electric current is applied via function generator 2802 described with reference to FIG. 28. The signal is tracked via development system 2800 (FIG. 28), wherein a tracking algorithm, which may include an adaptive filter, improves tracking of the applied electric current.

Returning to FIG. 30, then normal versus abnormal brain wave activity is processed (S3016).

Processing for normal versus abnormal brain wave activity is performed as described with reference to FIG. 11B. Feature vectors are developed for the brain waves and compared with normal and abnormal feature vectors in order to classify brain waves into normal and abnormal.

Returning to FIG. 30, then processed information is presented for viewing (S3018).

Computing device portion 810 (FIG. 8) presents a representation for the trajectory of the electrical current for viewing to user via presentation portion 816 (FIG. 8). For example, a person hears a noise and the information associated with the trajectory of the electrical current from the ear to the brain is presented for viewing. Furthermore, information associated with normal versus abnormal brain wave activity is presented for viewing. For example, a diagnosis as to whether a person is Epileptic or not may be determined. Furthermore, system determines whether a stimulus is received and is communicated to the correction in the brain. For example, a light may be presented to a person's eye and the path of the signal associated with the light is tracked as it travels within the brain. Based upon whether the signal is delivered to the correct location within the brain, a diagnosis may be performed with respect to normal or abnormal brain functioning.

Returning to FIG. 30, then method 3000 terminates execution (S3020).

FIG. 30 illustrates an example method for operation of an example MEG system where the system may be calibrated, algorithms developed, magnetic information plus noise may be received, filtered, processed and presented for viewing.

The present invention enables a MEG system that does not use SQUIDS and as a result is portable, uses less power is more economical for acquisition and operation and is less volatile. Furthermore, since MEG system is less volatile is requires less maintenance and costs associated with maintenance. Further, MEG system enables tracking of magnetic dipoles in a three dimensional volume as merely detecting the location of a magnetic dipole at a point or in a single plane.

Signals from the magnetometers may be processed via any known MEG processing system and method, non-limiting examples of which include those disclosed in: Medvedovsky et al., *Fine tuning the correlation limit of spatio-temporal signal space separation for magnetoencephalography, Journal of Neuroscience Methods*, 177, 2009, pp. 203-2011; Dale et al., *Spatiotemporal mapping of brain activity by integration of multiple imaging modalities, Cognitive neuroscience*, pp. 202-208; Bernd Lutkenhoner, *Magnetoencephaliography and its Achilles' heel, Journal of Physiology—Paris*, 97, 2003, pp. 641-658; Knappe et al, *Cross-validation of microfabricated atomic magnetometers with superconducting quantum interference devices for biomagnetic applications, Applied Physics Letters* 97, 133703 (2010).

Benefits of a MEG system in accordance with aspects of the present invention include: a) 3D localization and tracking, (especially inside the brain, e.g. as the signal travels from the eye—to the thalamus—to the cortex) in real time; b) ambient noise reduction, c) patient noise reduction, d) signal processing for causality and removal of degenerate answers, i.e. visualizing multiple dipoles and tracks, e) only about nine channels (three three-axis gradiometers) instead of hundreds of single channels, f) the use of magnetometers that operate at room temp without helium; g) auto-decision aids with the computer to not only diagnose traditional templates but also pathologies; all adding up to h) a transportable-mobile system.

With respect to 3D localization and tracking, a MEG system in accordance with aspects of the present invention can follow magnetic dipoles flowing through the brain. A MEG system in accordance with aspects of the present invention may find, or localize a neurological synaptic firing, just as a prior art MEG system—without the need of SQUIDS and all the problems associated therewith. Furthermore, a MEG system in accordance with aspects of the present invention can perform additional functions that prior art MEG systems cannot. For example, a MEG system in accordance with aspects of the present invention may follow neurological synaptic firings to track brain activity on a three dimensional basis. This aspect will enable further study of the brain.

With respect to ambient noise reduction, a MEG system in accordance with aspects of the present invention is able to detect and account for ambient noise. By using additional sensors to detect ambient parameters, non-limiting examples of which include additional magnetometers, photosensors, microphones, the detected ambient parameters may be addressed by known signal processing methods. Accordingly, a clear MEG signal may easily be obtained.

With respect to patient noise reduction, a MEG system in accordance with aspects of the present invention is able to detect and account for patient noise. By using additional sensors to detect patient parameters, non-limiting examples of which include accelerometers, EEGs, ECGs, biometric parameters of the patient may be monitored. For example, as mentioned previously, an accelerometer attached to the patients arm may detect motion of the arm. This motion will provide a corresponding brain signal. A MEG system in accordance with aspects of the present invention is able to account for the brain signal corresponding to the motion of the arm, and if required, subtract the signal corresponding to the arm motion.

A MEG system in accordance with aspects of the present invention may also perform signal processing for causality and removal of degenerate answers, i.e. visualizing multiple dipoles and tracks. In particular, multiple dipoles may be tracked in a three dimensional basis. The relationship of these multiple dipoles may then be studied, which was not possible with prior art MEG systems.

As mentioned previously with reference to FIG. 2A, some (more advanced) prior art MEG systems may use up to 100 gradiometers, i.e., up to 100 channels. A MEG system in accordance with aspects of the present invention, is able to localize and track a dipoles with merely nine channels—three three-axis gradiometers. Accordingly, a MEG system in accordance with aspects of the present invention is much less complex to build, is less expensive to maintain and easier to operate.

A MEG system in accordance with aspects of the present invention does not need SQUIDs. Accordingly, a MEG system in accordance with aspects of the present invention can operate at room temperature without the need of liquid helium, as required by conventional MEG systems. Accordingly, a MEG system in accordance with aspects of the present invention is much less complex to build, is less expensive to maintain and easier to operate.

A MEG system in accordance with aspects of the present invention can not only diagnose traditional templates but also pathologies. For example, known brain pathologies may have associated electrical (and therefore magnetic) signatures. By monitoring brain activity with a MEG system in accordance with aspects of the present invention, the brain wave signatures may be correlated with known pathological signatures to assist in diagnosis of patients.

A conventional MEG system is large, complex, and immobile. However, as a result of the simplistic design—three three-axis gradiometers that do not require super-cooling, a MEG system in accordance with aspects of the present invention is transportable.

It should be noted that the non-limiting example magnetometers discussed at length herein, those using loops to detect a magnetic field, are merely for purposes of discussion. As mentioned previously, any known type of magnetometer may be used, so long as a three-axis magnetometer is a result. The present invention may incorporate the addition of a single-axis gradiometer for noise reduction. In particular, many sensors may be used, which are able to sense a signal and noise fields along the same axis at a single position, to obtain a noise reduced "signal." However, a set of three three-axis gradiometers is used for localization and tracking a dipole three planes in accordance with the present invention. Another example magnetometer that may be used with aspects of the present invention is disclosed by Schwindt, *Chip-scale atomic magnetometer, Applied Physics Letters*, vol. 85, Num. 26, 27 Dec. 2004.

The foregoing description of various preferred embodiments of the invention have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A magnetoencephalography system for use with a head, said magnetoencephalography system comprising:
    a shell having an outer surface and an inner surface, said inner surface being shaped to surround the head;
    a first three-axis gradiometer operable to detect a first magnetic field vector from a magnetic dipole in the head and to generate a first detected signal based on the first magnetic field vector, said first three-axis gradiometer being disposed at a first position of said inner surface;
    a second three-axis gradiometer operable to detect a second magnetic field vector from the magnetic dipole in the head and to generate a second detected signal based on the second magnetic field vector, said second three-axis gradiometer being disposed at a second position of said inner surface;
    a third three-axis gradiometer operable to detect a third magnetic field vector from the magnetic dipole in the head and to generate a third detected signal based on the third magnetic field vector, said third three-axis gradiometer being disposed at a third position of said inner surface;
    a noise reference sensor configured to detect ambient noise; and
    a computing portion comprising at least a processor configured to:
        remove ambient noise; and
        determine a location of the magnetic dipole based on the first detected signal, the second detected signal and the third detected signal,
    wherein at least one three-axis gradiometer of the first, second, and third three-axis gradiometers does not include a superconducting device;
    wherein each of the first three-axis gradiometer, the second three-axis gradiometer, and the third three-axis gradiometer comprise a first detection portion, a second detection portion and a third detection portion; and
    wherein the first detection portion, the second detection portion, and the third detection portion are parallel to each other.

2. The magnetoencephalography system of claim 1, wherein said first detection portion, said second detection portion, and said third detection portion are disposed on an x-y plane,
    wherein said first detection portion is separated from said second detection portion by a first distance in an x direction, and
    wherein said second detection portion is separated from said third detection portion by second distance in a y direction.

3. The magnetoencephalography system of claim 2, further comprising a calibrated magnetic dipole disposed at said inner surface and being operable to provide a calibrated magnetic field to said first three-axis gradiometer, said second three-axis gradiometer and said third three-axis gradiometer.

4. The magnetoencephalography system of claim 1, further comprising a magnetic dipole disposed at said inner surface and being operable to provide a magnetic field to said first three-axis gradiometer, said second three-axis gradiometer and said third three-axis gradiometer.

5. The magnetoencephalography system of claim 1, wherein said computing portion is further configured to monitor at least one of Beta waves, Alpha waves, Occipital waves, Theta waves and Delta waves in the head based on the first detected signal, the second detected signal and the third detected signal.

6. The magnetoencephalography system of claim 1, wherein the first three-axis gradiometer, the second three-axis gradiometer, and the third three-axis gradiometer do not include superconductor device.

7. The magnetoencephalography system of claim 1, wherein the magnetoencephalography system does not include more than three three-axis gradiometers.

8. The magnetoencephalography system of claim 1, wherein the magnetoencephalography system is portable.

9. A magnetoencephalography method for detecting magnetic fields in a head, said magnetoencephalography method comprising:
    surrounding the head with a device including a shell, a first three-axis gradiometer, a second three-axis gradiometer, a third three-axis gradiometer, and a noise reference sensor, the shell having an outer surface and an inner surface, the inner surface being shaped to surround the head, the first three-axis gradiometer being disposed at a first position of the inner surface, the second three-axis gradiometer being disposed at a second position of the inner surface and the third three-axis gradiometer being disposed at a third position of the inner surface;
    detecting, via the first three-axis gradiometer, a first magnetic field vector from a magnetic dipole in the head;
    generating, via the first three-axis gradiometer, a first detected signal based on the first magnetic field vector;
    detecting, via the second three-axis gradiometer, a second magnetic field vector from the magnetic dipole in the head; generating, via the second three-axis gradiometer, a second detected signal based on the second magnetic field vector;
    detecting, via the third three-axis gradiometer, a third magnetic field vector from the magnetic dipole in the head;

generating, via the third three-axis gradiometer, a third detected signal based on the first magnetic field vector;

detecting, via the noise reference sensor, ambient noise;

removing, via a configured computing portion, the ambient noise; and determining, via a configured computing portion comprising at least a processor, a location of the magnetic dipole based on the first detected signal, the second detected signal and the third detected signal, wherein at least one three-axis gradiometer of the first, second, and third three-axis gradiometers does not include a superconducting device;

wherein each of the first three-axis gradiometer, the second three-axis gradiometer, and the third three-axis gradiometer comprise a first detection portion, a second detection portion and a third detection portion; and wherein the first detection portion, the second detection portion, and the third detection portion are parallel to each other.

10. The magnetoencephalography method of claim 9, wherein said detecting, via the first three-axis gradiometer, a first magnetic field vector from a magnetic dipole in the head comprises detecting, via the first three-axis gradiometer that includes the first detection portion, the second detection portion, and the third detection portion, wherein the first detection portion, the second detection portion and the third detection portion are disposed on an x-y plane, wherein the first detection portion is separated from the second detection portion by a first distance in an x direction, and wherein the second detection portion is separated from the third detection portion by a second distance in a y direction.

11. The magnetoencephalography method of claim 10, wherein said surrounding the head with the device including the shell, the first three-axis gradiometer, the second three-axis gradiometer, the third three-axis gradiometer, and the noise reference sensor further comprises surrounding the head with the device further including a calibrated magnetic dipole disposed at the inner surface and being operable to provide a calibrated magnetic field to the first three-axis gradiometer, the second three-axis gradiometer and the third three-axis gradiometer.

12. The magnetoencephalography method of claim 9, wherein said surrounding the head with the device including the shell, the first three-axis gradiometer, the second three-axis gradiometer, the third three-axis gradiometer, and the noise reference sensor further comprises surrounding the head with the device further including a magnetic dipole disposed at the inner surface and being operable to provide a magnetic field to the first three-axis gradiometer, the second three-axis gradiometer and the third three-axis gradiometer.

13. The magnetoencephalography method of claim 9, further comprising monitoring, via the configured computing portion, at least one of Beta waves, Alpha waves, Occipital waves, Theta waves and Delta waves in the head based on the first detected signal, the second detected signal and the third detected signal.

14. The magnetoencephalography method of claim 9, wherein surrounding the head with the device including the shell, the first three-axis gradiometer, the second three-axis gradiometer, the third three-axis gradiometer, and the noise reference sensor comprises surrounding the head with the device including the shell, the first three-axis gradiometer, the second three-axis gradiometer, the third three-axis gradiometer, and the noise reference sensor such that the first three-axis gradiometer, the second three-axis gradiometer, and the third three-axis gradiometer do not include superconductor device.

15. The magnetoencephalography method of claim 9, wherein surrounding the head with the device including the shell, the first three-axis gradiometer, the second three-axis gradiometer, the third three-axis gradiometer, and the noise reference sensor comprises surrounding the head with the device consisting of the shell, the first three-axis gradiometer, the second three-axis gradiometer, the third three-axis gradiometer, and the noise reference sensor.

16. The magnetoencephalography method of claim 9, wherein surrounding the head with the device including the shell, the first three-axis gradiometer, the second three-axis gradiometer, the third three-axis gradiometer, and the noise reference sensor comprises surrounding the head with the device including the shell, the first three-axis gradiometer, the second three-axis gradiometer, the third three-axis gradiometer, and the noise reference sensor such that the device is portable.

* * * * *